United States Patent
Coffey et al.

(10) Patent No.: US 8,470,312 B2
(45) Date of Patent: *Jun. 25, 2013

(54) ABROGATING PROINFLAMMATORY CYTOKINE PRODUCTION DURING ONCOLYTIC REOVIRUS THERAPY

(75) Inventors: Matthew C. Coffey, Calgary (CA); Bradley G. Thompson, Calgary (CA); Hardev Pandha, Surrey (GB)

(73) Assignee: Oncolytics Biotech, Inc., Calgary, AB (CA)

( * ) Notice: Subject to any disclaimer, the term of this patent is extended or adjusted under 35 U.S.C. 154(b) by 104 days.

This patent is subject to a terminal disclaimer.

(21) Appl. No.: 12/994,114

(22) PCT Filed: May 27, 2009

(86) PCT No.: PCT/CA2009/000721
§ 371 (c)(1),
(2), (4) Date: Nov. 22, 2010

(87) PCT Pub. No.: WO2009/143611
PCT Pub. Date: Dec. 3, 2009

(65) Prior Publication Data
US 2011/0070200 A1 Mar. 24, 2011

Related U.S. Application Data

(60) Provisional application No. 61/056,292, filed on May 27, 2008, provisional application No. 61/113,791, filed on Nov. 12, 2008.

(51) Int. Cl.
*A61K 5/00* (2006.01)
*A61K 48/00* (2006.01)

(52) U.S. Cl.
USPC ..................................... 424/93.3; 424/215.1

(58) Field of Classification Search
None
See application file for complete search history.

(56) References Cited

U.S. PATENT DOCUMENTS

| | | |
|---|---|---|
| 4,554,101 A | 11/1985 | Hopp |
| 5,023,252 A | 6/1991 | Hseih |
| 6,110,461 A | 8/2000 | Lee et al. |
| 6,136,307 A | 10/2000 | Lee et al. |
| 6,261,555 B1 | 7/2001 | Lee et al. |
| 6,344,195 B1 | 2/2002 | Lee et al. |
| 6,455,038 B1 * | 9/2002 | Lee et al. ..................... 424/93.6 |
| 6,528,305 B2 | 3/2003 | Thompson et al. |
| 6,565,831 B1 | 5/2003 | Coffey et al. |
| 6,576,234 B2 | 6/2003 | Lee et al. |
| 6,808,916 B2 | 10/2004 | Coffey et al. |
| 6,811,775 B2 | 11/2004 | Lee et al. |
| 7,014,847 B2 | 3/2006 | Coffey et al. |
| 7,049,127 B2 | 5/2006 | Thompson et al. |
| 7,052,832 B2 | 5/2006 | Coffey |
| 7,186,542 B2 | 3/2007 | Coffey et al. |
| 7,264,798 B2 * | 9/2007 | Coffey et al. ................ 424/93.6 |
| 7,306,902 B2 | 12/2007 | Thompson et al. |
| 7,374,752 B2 * | 5/2008 | Lee et al. ..................... 424/93.2 |
| 7,708,987 B2 * | 5/2010 | Coffey et al. ................ 424/93.2 |
| 7,803,385 B2 * | 9/2010 | Coffey ........................ 424/215.1 |
| 7,815,914 B2 * | 10/2010 | Coffey ........................ 424/204.1 |
| 7,964,187 B2 * | 6/2011 | Coffey et al. ................ 424/93.6 |
| 8,066,985 B2 * | 11/2011 | Lee et al. ................... 424/93.21 |
| 8,071,087 B2 * | 12/2011 | Lee et al. ..................... 424/93.3 |
| 2002/0168344 A1 | 11/2002 | Coffey et al. |
| 2003/0165465 A1 | 9/2003 | Roberts et al. |
| 2008/0292594 A1 | 11/2008 | Coffey et al. |
| 2009/0117082 A1 * | 5/2009 | Lee et al. ..................... 424/93.6 |
| 2012/0141426 A1 * | 6/2012 | Lee et al. ..................... 424/93.6 |

FOREIGN PATENT DOCUMENTS

| | | | |
|---|---|---|---|
| WO | WO99/18799 A1 * | 4/1999 | |
| WO | 02066040 | 8/2002 | |

OTHER PUBLICATIONS

Bilenker et al. Clinical Cancer Research 2005, vol. 11, pp. 1527-1533.*
Kehoe et al. Br. J. Cancer, 1992, vol. 66 (4), pp. 717-719.*
Barbacid, ras Genes, Ann. Rev. Biochem, 56:779-827 (1987).
Brose et al., BRAF and RAS Mutations in Human Lung Cancer and Melanoma, Cancer Res., 62:6997-7000 (2002).
Chandran et al., Protease Cleavage of Reovirus Capsid Protein μ1/μ1C Is Blocked by Alkyl Sulfate Detergents, Yielding a New Type of Infectious Subvirion Particle, J. of Virology, 72(1):467-475 (1998).
Heinemann et al., Synergistic Antitumour Activity of Oncolytic Reovirus and Cisplatin in Malignant Melanoma, 4th International Conference on Oncolytic Viruses (online poster) (2007).
Kobayashi et al., A Plasmid-Based Reverse Genetics System for Animal Double-Stranded RNA Viruses, Cell Host & Microbe, 1:147-157 (2007).
Qiao et al., Cyclophosphamide Facilitates Antitumor Efficacy against SubcutaneousTumors following Intravenous Delivery of Reovirus, Clin. Cancer Res., 14(1):259-269 (2008).
Smith et al., Polypeptide Components of Virions, Top Component and Cores of Reovirus Type 3, Virology, 39 (4):791-810 (1969).
Strong et al., The Molecular Basis of Viral Oncolysis: Usurpation of the RAS Signaling Pathway by Reovirus, EMBO J., 17(12):3351-3362 (1998).
Wiesmuller et al., Signal Transduction Pathways Involving RAS Mini Review, Cellular Signaling, 6(3):247-267 (1994).
Sei S et al "Synergistic antitumor activity of oncolytic reovirus and chemotherapeutic agents against non-small cell lung cancer (NSCLC)", EJC Supplements, 4(12):103 (2006), 18th Symposium on Molecular Targets and Cancer Therapeutics; Prague, Czech Republic; Nov. 7-10, 2006 [abstract].

(Continued)

*Primary Examiner* — Bao Li
(74) *Attorney, Agent, or Firm* — Kilpatrick, Townsend & Stockton LLP

(57) ABSTRACT

Provided herein are methods for treating a proliferative disorder in a subject comprising administering to the subject one or more reoviruses and one or more agents that modulate expression or activity of pro-inflammatory cytokines. For example, the agents may inhibit expression or activity of pro-inflammatory cytokines.

20 Claims, 6 Drawing Sheets

OTHER PUBLICATIONS

Smakman Niels et al "KRAS (D13) promotes apoptosis of human colorectal tumor cells by Reovirus T3D and oxaliplatin but not by tumor necrosis factor-related apoptosis-inducing ligand", Cancer Research, 66 (10):5403-5408 (2006).

Heinemann L et al "308 Poster Synergistic anti-tumour activity of oncolytic Reovirus and cisplatin in a B16.F10 mouse melanoma model", European Journal of Cancer. Supplement, Pergamon, Oxford, GB, 6(12):99 (2008) [abstract].

Steven M. Opal, et al., "Anti-Inflammatory Cytokines", Chest 117:1162-1172 (2000).

* cited by examiner

ABROGATING PROINFLAMMATORY CYTOKINE PRODUCTION DURING ONCOLYTIC REOVIRUS THERAPY

BACKGROUND

Reovirus is a dsRNA virus with tropism to cancer cells having an activated Ras pathway. It has been demonstrated that administration of reovirus into tumor bearing animals results in generation of a robust anti-viral response mediated by both the humoral and cellular arms of the immune system. This anti-viral response can antagonize the oncolytic effectiveness of the therapeutic virus. As such, combinational use of immune suppressing agents to overcome this immune antagonism of reovirus oncolysis has been explored. It has been demonstrated that co-administration of agents that ablate the generation of neutralizing anti-reovirus antibodies (NARA) can result in morbidity in the test animals. The response in the test animals has been characterized by reovirus replication outside of the target tumor tissues, suggesting that humoral immunity serves a protective role in preventing reovirus infection of the host (Qiao et al., Clin. Cancer Res. 14(1):259-69 (2008)).

SUMMARY

Provided herein are methods for treating a proliferative disorder in a subject comprising administering to the subject one or more reoviruses and one or more agents that modulate expression or activity of pro-inflammatory cytokines. For example, the agents may inhibit expression or activity of pro-inflammatory cytokines.

The details of one or more aspects are set forth in the accompanying drawings and description below. Other features, objects, and advantages will be apparent from the description and drawings, and from the claims.

DETAILED DESCRIPTION

Figure 1A:
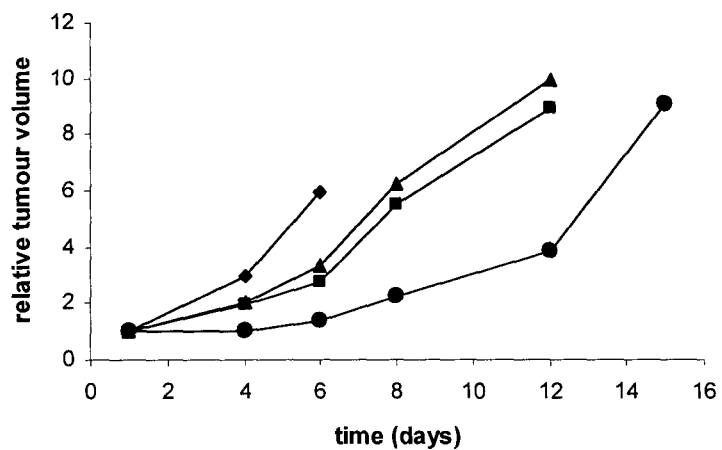
FIGS. 1A, 1B, 1C and 1D show reduced tumor growth and increased survival following reovirus/cisplatin combination therapy. C57Bl/6 (FIGS. 1A and 1C) and C3H (FIGS. 1B and 1D) mice bearing subcutaneous B16.F10 and K1735 tumors, respectively, were treated on days 1 and 4 with either reovirus alone via intratumoral (i.t.) injection (squares), cisplatin alone via intraperitoneal (i.p.) administration (triangles), or reovirus and cisplatin in combination (circles). Control treated mice (diamonds) received PBS. Tumors were measured on the days indicated and tumor volume expressed as tumor volume relative to volume at commencement of treatment (FIGS. 1A and 1B). Mice were euthanized when tumors exceeded 15 mm in any one dimension. Survival is expressed as Kaplan-Myer plots (FIGS. 1C and 1D).

As described previously (see, for example, U.S. Pat. Nos. 6,110,461; 6,136,307; 6,261,555; 6,344,195; 6,576,234; and 6,811,775), reoviruses use a host cell's Ras pathway machinery to downregulate double-stranded RNA-activated protein kinase (PKR) and thus replication in the cell. Based upon these discoveries, methods have been developed for using reoviruses to treat proliferative disorders. It has been demonstrated that reovirus therapy results in release of pro-inflammatory cytokines. The pro-inflammatory cytokines antagonize reovirus infection and reovirus spread into the tumor tissue. The protective function of the humoral arm of the immune system in preventing reovirus toxicity has been further suggested by the observation that while, athymic mice manifest no morbidity to reovirus infection, SC1D mice and B-cell knock-out animals invariably die from reovirus infection.

Reovirus oncolysis can be enhanced in vitro by the use of cytotoxic agents. Surprisingly, as described herein, the combinational use of platinum compounds does not impact the production of NARA but has a profound effect on the production of pro-inflammatory cytokines including: IL-1I, IL-3, IL-6, IL-12 p70, IL-17, MIP-1I, and RANTES. Inhibition of pro-inflammatory cytokines by cisplatin prevents T-cell recognition of reovirus infected cells and allows virus replication to ensue without cellular immunity antagonism. However, cisplatin allows production of protective neutralizing anti-reovirus antibodies (NARA) NARA and its concomitant benefits (e.g., preventing reovirus toxicities in patients). The use of platinum compounds to selectively block both innate and adaptive T-cell responses, while having no effect on B-cell activity, has not previously been described.

Provided herein is a method of treating a proliferative disorder in a subject comprising administering a reovirus to the subject and administering to the subject an agent that modulates pro-inflammatory cytokines.

For example, the agent inhibits the expression or activity of the pro-inflammatory cytokines. As used herein, the term modulate refers to a change (positive or negative) of 10, 20, 30, 40, 50, 60, 70, 80, 90 percent or greater as compared to a control level. As used herein, control refers to a reference standard from an untreated sample or subject. By way of example, a control level is the level of expression or activity in a control sample in the absence of a stimulus. The control can be prior to, after recovery, or without the stimulus.

Optionally, the cytokine modulating agent blocks T-cell responses while having little to no effect on B-cell activity. Thus, the agent inhibits pro-inflammatory cytokines but does not inhibit or minimally inhibits production of NARA. Optionally, the agent is a platinum compound. Suitable platinum compounds include, but are not limited to, cisplatin, carboplatin, metaplatin and oxaliplatin.

Other agents that inhibit pro-inflammatory cytokines include, but are not limited to, TNF-I antibodies such as infliximab, CDP571, CDP870, and adalimumab; recombinant, human soluble p55 TNF receptors such as onercept; soluble TNF receptor and Fc fragment fusion proteins such as etanercept; pegylated Fab fragments of humanized antibody to TNF such as certolizumab pegol; chimeric antibodies to anti-I chain of IL-2 receptor such as basiliximab or daclizumab; IL-12p40 antibodies such as ABT-874; IL-6 receptor antibodies such as MRA or tocilizumab; IFN-K antibodies such as fontolizumab; antibodies that inhibit IL-1 binding to the IL-1 receptor such as AMG108; caspase-1 inhibitors that inhibit cytokine-release such as diarylsulphonylurene; IL-15 antibodies such as mepolizumab; IL-8 antibodies such as ABX-IL-8; IL-9 antibodies including IL-9 monoclonal antibodies; recombinant human IL-21 also referred to as 494C10; inhibitors of TNF-I, IL-1θ, IL-6 and granulocyte monocyte-colony stimulating factor expression such as biophylum sensitivum; NF-PB signaling blockers that inhibit pro-inflammatory cytokine expression such as simvastatin; and inhibitors of IL-6 expression and NF-PB activation such as (−)-epigallocatechin-3-gallate (EGCG).

Other agents include human recombinant lactoferrin, which inhibits cellular release of proinflammatory cytokines and prometastatic cytokines (including IL-6, IL-8, granulocyte macrophage colony-stimulating factor and TNF-α). Inhibitors of dendritic cell derived IL-12 and IL-18 such as rapamycin and sanglifehrin are also suitable for use in the provided methods. Rapamycin is an immunosuppressant that inhibits T cell mTOR kinase activation, and Sanglifehrin A is a cyclophilin-binding immunosuppressant that also inhibits IL-2 dependent T cell proliferation. Also suitable for use in the provided methods is dietary rutin colitis, which suppresses the induction of pro-inflammatory cytokines such as IL-1β, IL-6, and GM-CS.

Optionally, the method further includes selecting a subject with a proliferative disorder, wherein the subject is in need of inhibition of a pro-inflammatory cytokine response. For example, such a subject may include a subject with little response to reovirus alone or with a progressive resistance to reovirus therapy.

As used herein, the term proliferative disorder refers to any cellular disorder in which the cells proliferate more rapidly than normal tissue growth. A proliferative disorder includes, but is not limited to, neoplasms, which are also referred to as tumors. A neoplasm can include, but is not limited to, pancreatic cancer, breast cancer, brain cancer (e.g., glioblastoma), lung cancer, prostate cancer, colorectal cancer, thyroid cancer, renal cancer, adrenal cancer, liver cancer, neurofibromatosis 1, and leukemia. A neoplasm can be a solid neoplasm (e.g., sarcoma or carcinoma) or a cancerous growth affecting the hematopoietic system (e.g., lymphoma or leukemia). Other proliferative disorders include, but are not limited to, neurofibromatosis.

Generally, in proliferating disorders for which reovirus is used as a treatment, at least some of the proliferating cells associated with the disorder may have a mutation in which the Ras gene (or an element of the Ras signaling pathway) is activated, either directly (e.g., by an activating mutation in Ras) or indirectly (e.g., by activation of an upstream or downstream element in the Ras pathway). Activation of an upstream element in the Ras pathway includes, for example, transformation with epidermal growth factor receptor (EGFR) or Sos. See, for example, Wiessmuller and Wittinghofer, 1994, *Cellular Signaling* 6(3):247-267; and Barbacid, 1987, *Ann. Rev. Biochem.* 56, 779-827. Activation of a downstream element in the Ras pathway includes, for example, mutation within B-Raf. See, for example, Brose et al., 2002, *Cancer Res.* 62:6997-7000. A proliferative disorder that results, at least in part, by the activation of ras, an upstream element of ras, or an element in the ras signaling pathway is referred to herein as a ras-mediated proliferative disorder. In addition, the reovirus is useful for treating proliferative disorders caused by mutations or dysregulation of PKR. See, for example, Strong et al., 1998, *EMBO J.* 17:3351-62.

Optionally, the provided methods further comprise the step of selecting a subject with a ras-mediated proliferative disorder. Optionally, the provided methods comprise the step of determining whether the proliferative disorder is a ras-mediated proliferative disorder. Such methods for determining whether a proliferative disorder has a certain phenotype are known. See, for example, U.S. Pat. No. 7,306,902, which is incorporated herein by reference in its entirety.

As used herein, reovirus refers to any virus classified in the reovirus genus, whether naturally occurring, modified, or recombinant. Reoviruses are viruses with a double-stranded, segmented RNA genome. The virions measure 60-80 nm in diameter and possess two concentric capsid shells, each of which is icosahedral. The genome consists of double-stranded RNA in 10-12 discrete segments with a total genome size of 16-27 kbp. The individual RNA segments vary in size. Three distinct but related types of reoviruses have been recovered from many species. All three types share a common complement-fixing antigen.

The human reovirus includes three serotypes: type 1 (strain Lang or T1L), type 2 (strain Jones, T2J), and type 3 (strain Dearing or strain Abney, T3D). The three serotypes are easily identifiable on the basis of neutralization and hemagglutinin-inhibition assays. A reovirus according to this disclosure can be a type 3 mammalian orthoreovirus. Type 3 mammalian orthoreoviruses include, without limitation, Dearing and Abney strains (T3D or T3A, respectively). See, for example, ATCC Accession Nos. VR-232 and VR-824.

The reovirus may be naturally occurring or modified. The reovirus is naturally-occurring when it can be isolated from a source in nature and has not been intentionally modified by humans in the laboratory. For example, the reovirus can be from a field source, that is, from a human who has been infected with the reovirus. The reovirus may also be selected or mutagenized for enhanced oncolytic activity.

The reovirus may be modified but still capable of lytically infecting a mammalian cell having an active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandran and Nibert, J. of Virology 72(1):467-75 1998). For example, the virion may be treated with chymotrypsin in the presence of micelle-forming concentrations of alkyl sulfate detergents to generate a new infectious subviral particle (ISVP).

The reovirus may be a recombinant reovirus. For example, the recombinant reovirus can be a reassortant reovirus, which includes genomic segments from two or more genetically distinct reoviruses. Reassortment of reovirus genomic segments may occur following infection of a host organism with at least two genetically distinct reoviruses. Reassortment of viruses can be generated in cell culture, for example, by co-infection of permissive host cells with genetically distinct reoviruses. Accordingly, the provided methods include the use of a recombinant reovirus resulting from reassortment of genome segments from two or more genetically distinct reoviruses, including but not limited to, human reovirus, such as type 1 (e.g., strain Lang), type 2 (e.g., strain Jones), and type 3 (e.g., strain Dearing or strain Abney); non-human mammalian reoviruses; or avian reovirus. Recombinant reovirus can also be made by genetic engineering, chemically synthesized, or treatment with chemical or physical mutagens. Optionally, the provided methods include the use of recombinant reoviruses resulting from reassortment of genome segments from two or more genetically distinct reoviruses wherein at least one parental virus is genetically engineered, comprises one or more chemically synthesized genomic segment, has been treated with chemical or physical mutagens, or is itself the result of a recombination event. Optionally, the provided methods include the use of the recombinant reovirus that has undergone recombination in the presence of chemical mutagens, including but not limited to, dimethyl sulfate and ethidium bromide, or physical mutagens, including but not limited to, ultraviolet light and other forms of radiation.

Optionally, the provided methods include the use of reoviruses with mutations (including insertions, substitutions, deletions or duplications) in one or more genome segments. Such mutations can comprise additional genetic information as a result of recombination with a host cell genome or can comprise synthetic genes. For example, mutant reoviruses as described herein can contain a mutation that reduces or essentially eliminates expression of a sigma3 polypeptide or that results in the absence of a functional sigma3 polypeptide as described in U.S. Ser. No. 12/124,522, which is incorporated by reference herein in its entirety. A mutation that eliminates expression of a sigma3 polypeptide or that results in the absence of a functional sigma3 polypeptide can be in the nucleic acid encoding the sigma3 polypeptide (i.e., the S4 gene) or in a nucleic acid that encodes a polypeptide that regulates the expression or function of the sigma3 polypeptide.

As used herein, a mutation that reduces the expression of a sigma3 polypeptide refers to a mutation that results in a decrease in the amount of sigma3 polypeptides, compared to a reovirus expressing wild type levels of sigma3 polypeptide, of at least 30% (e.g., at least 40%, 50%, 60%, 70%, 80%, 90%, or 95%). As used herein, a mutation that essentially eliminates expression of a sigma3 polypeptide refers to a mutation that results in a decrease in the amount of sigma3 polypeptides, relative to the amount of sigma3 polypeptides produced by a wild type reovirus, of at least 95% (e.g., 96%, 97%, 98%, 99%, or 100%). As used herein, a mutation that results in a decrease in or absence of a functional sigma3 polypeptide refers to a mutation that allows expression of the sigma3 polypeptide but that results in a sigma3 polypeptide that is not able to assemble or incorporate into the viral capsid. It would be understood that it may be desirable or necessary for sigma3 polypeptides to retain other functionalities (e.g., the ability to bind RNA) in order that the mutant reovirus retain the ability to propagate.

A mutation in a sigma3 polypeptide as described herein can result in a sigma3 polypeptide that is incorporated into the capsid at levels that are reduced relative to a sigma3 polypeptide that does not contain the mutation (e.g., a wild type sigma3 polypeptide). A mutation in a sigma3 polypeptide as described herein also can result in a sigma3 polypeptide that cannot be incorporated into a viral capsid. Without being bound by any particular mechanism, a sigma3 polypeptide may have reduced function or lack function due, for example, to an inability of the sigma3 polypeptide and the mu1 polypeptide to bind appropriately, or due to a conformational change that reduces or prohibits incorporation of the sigma3 polypeptide into the capsid.

In addition to a mutation that abolishes or reduces expression of the sigma3 polypeptide or that results in a non-functional or reduced-function sigma3 polypeptide, a mutant reovirus as described herein also can contain one or more further mutations (e.g., a second, third, or fourth mutation) in one of the other reovirus capsid polypeptides (e.g., mu1, lambda2, and/or sigma1). Reoviruses containing a mutation affecting the sigma3 polypeptide and, optionally, a further mutation in any or all of the other outer capsid proteins can be screened for the ability of such mutant reoviruses to infect and cause lysis of cells. For example, neoplastic cells that are resistant to lysis by wild type reovirus can be used to screen for effective mutant reoviruses described herein.

For example, a further mutation can reduce or essentially eliminate expression of a mu1 polypeptide or result in the absence of a functional mu1 polypeptide. The mu1 polypeptide, which is encoded by the M2 gene, is likely involved in cell penetration and may play a role in transcriptase activation. Each virion contains about 600 copies of mu1 polypeptides, which are present in the form of 1:1 complexes with sigma3 polypeptides. The mu1 polypeptide is myristolated on its N-terminus, and then the myristolated N-terminal 42 residues are cleaved off, resulting in a C-terminal fragment (mu1C). Additionally or alternatively, a further mutation can reduce or essentially eliminate expression of a lambda2 polypeptide or result in the absence of a functional lambda2 polypeptide, and/or a further mutation can reduce or essentially eliminate expression of a sigma1 polypeptide or result in the absence of a functional sigma1 polypeptide. The lambda2 polypeptide is encoded by the L2 gene and is involved in particle assembly, and exhibits guanylyltransferase and methyltransferase activity. The sigma1 polypeptide is encoded by the S1 gene and is involved in cell-attachment and serves as the viral hemagglutinin.

For example, the reovirus has a lambda-3 polypeptide having one or more amino acid modifications; a sigma-3 polypeptide having one or more amino acid modifications; a mu-1 polypeptide having one or more amino acid modifications; and/or a mu-2 polypeptide having one or more amino acid modifications, as described in U.S. Ser. No. 12/046,095, which is incorporated by reference herein in its entirety. By way of example, the one or more amino acid modifications in the lambda-3 polypeptide are a Val at residue 214, an Ala at residue 267, a Thr at residue 557, a Lys at residue 755, a Met at residue 756, a Pro at residue 926, a Pro at residue 963, a Leu at residue 979, an Arg at residue 1045, a Val at residue 1071, or any combination thereof, numbered relative to GenBank Accession No. M24734.1. It is noted that, when the amino acid sequence is a Val at residue 214 or a Val at residue 1071, the amino acid sequence further includes at least one additional change in the amino acid sequence. Optionally, the lambda-3 polypeptide includes the sequence shown in SEQ ID NO:18. Further by way of example, the one or more amino acid modifications in the sigma-3 polypeptide are a Leu at residue 14, a Lys at residue 198, or any combination thereof, numbered relative to GenBank Accession No. K02739. It is noted that, when the amino acid sequence is a Leu at residue 14, the amino acid sequence further includes at least one additional change in the amino acid sequence. Optionally, the sigma-3 polypeptide includes the sequence shown in SEQ ID NO:14. Further by way of example, the one or more amino acid modifications in the mu-1 polypeptide is an Asp at residue 73 numbered relative to GenBank Accession No. M20161.1. Optionally, the mu-1 polypeptide includes the sequence shown in SEQ ID NO:16. Also by way of example, the amino acid modification mu-2 polypeptide is a Ser at residue 528 numbered relative to GenBank Accession No. AF461684.1. Optionally, the mu-1 polypeptide includes the sequence shown in SEQ ID NO:15. A reovirus as described herein having one or more modifications can further include a reovirus sigma-2 polypeptide. Such a sigma-2 polypeptide has a Cys at one or more of position 70, 127, 195, 241, 255, 294, 296, or 340, numbered relative to GenBank Accession No. NP_694684.1. Optionally, the sigma-2 polypeptide includes the sequence shown in SEQ ID NO:12.

Optionally, the reovirus has a L1 genome segment having one or more nucleic acid modifications; a S4 genome segment having one or more nucleic acid modifications; a M1 genome segment having one or more nucleic acid modifications; and/or a M2 genome segment having one or more nucleic acid modifications, as described in U.S. Ser. No. 12/046,095, which is incorporated by reference herein in its entirety. By way of example, the one or more nucleic acid modifications in the L1 genome segment are a T at position 660, a G at position 817, an A at position 1687, a G at position 2283, an ATG at positions 2284-2286, a C at position 2794, a C at position 2905, a C at position 2953, an A at position 3153, or a G at position 3231, numbered relative to GenBank Accession No. M24734.1. Optionally, the L1 genome segment includes the sequence shown in SEQ ID NO:8. Further by way of example, the one or more nucleic acid modifications in the S4 genome segment is an A at position 74 and an A at position 624, numbered relative to GenBank Accession No. K02739. Optionally, the S4 genome segment includes the sequence shown in SEQ ID NO:4. Further by way of example, the nucleic acid modification in the M2 genome segment can be a C at position 248, numbered relative to GenBank Accession No. M20161.1. In one embodiment, the M2 genome segment includes the sequence shown in SEQ ID NO:6. Also by way of example, the nucleic acid modification in the M1 genome segment is a T at position 1595, numbered relative to GenBank Accession No. AF461684.1. Optionally, the M1 genome segment includes the sequence shown in SEQ ID NO:5. A reovirus as described herein can include any modification or combination of modifications disclosed herein. Optionally, a reovirus as described herein includes genomic segments having the sequences shown in SEQ ID NOs: 1-10 or the polypeptides shown in SEQ ID NOs: 11, 12, and 16-21, and either or both SEQ ID NO:13 or 14. Optionally, a reovirus as disclosed herein is identified as IDAC Accession No. 190907-01 which was deposited with the International Depositary Authority of Canada (IDAC, National Microbiology Laboratory, Public Health Agency of Canada, 1015 Arlington St., Winnipeg, Manitoba Canada R3E 3R2) on Sep. 19, 2007, and assigned Accession No. 190907-01.

A mutation or modification as referred to herein can be a substitution, insertion or deletion of one or more nucleotides. Point mutations include, for example, single nucleotide transitions (purine to purine or pyrimidine to pyrimidine) or transversions (purine to pyrimidine or vice versa) and single- or multiple-nucleotide deletions or insertions. A mutation in a nucleic acid can result in one or more conservative or non-conservative amino acid substitutions in the encoded polypeptide, which may result in conformational changes or loss or partial loss of function, a shift in the reading frame of translation (frame-shift) resulting in an entirely different polypeptide encoded from that point on, a premature stop codon resulting in a truncated polypeptide (truncation), or a mutation in a reovirus nucleic acid may not change the encoded polypeptide at all (silent or nonsense). See, for example, Johnson and Overington, 1993, *J. Mol. Biol.* 233: 716-38; Henikoff and Henikoff, 1992, *Proc. Natl. Acad. Sci. USA* 89:10915-19; and U.S. Pat. No. 4,554,101 for disclosure on conservative and non-conservative amino acid substitutions.

Mutations can be generated in the nucleic acid of a reovirus using any number of methods known in the art. For example, site directed mutagenesis can be used to modify a reovirus nucleic acid sequence. One of the most common methods of site-directed mutagenesis is oligonucleotide-directed mutagenesis. In oligonucleotide-directed mutagenesis, an oligonucleotide encoding the desired change(s) in sequence is annealed to one strand of the DNA of interest and serves as a primer for initiation of DNA synthesis. In this manner, the oligonucleotide containing the sequence change is incorporated into the newly synthesized strand. See, for example, Kunkel, 1985, *Proc. Natl. Acad. Sci. USA* 82:488; Kunkel et al., 1987, *Meth. Enzymol.* 154:367; Lewis and Thompson, 1990, *Nucl. Acids Res.* 18:3439; Bohnsack, 1996, *Meth. Mol. Biol.* 57:1; Deng and Nickoloff, 1992, *Anal. Biochem.* 200: 81; and Shimada, 1996, *Meth. Mol. Biol.* 57:157. Other methods are used routinely in the art to modify the sequence of a protein or polypeptide. For example, nucleic acids containing a mutation can be generated using PCR or chemical synthesis, or polypeptides having the desired change in amino acid sequence can be chemically synthesized. See, for example, Bang and Kent, 2005, *Proc. Natl. Acad. Sci. USA* 102:5014-9 and references therein.

Nucleic acids from reovirus particles can be isolated using standard commercially available nucleic acid methodology. See also, for example, Schiff et al., "Orthoreoviruses and Their Replication," Ch 52, in *Fields Virology*, Knipe and Howley, eds., 2006, Lippincott Williams and Wilkins. As used herein, isolated nucleic acids refer to nucleic acids that are separated from other nucleic acids with which they are usually associated. Thus, an isolated nucleic acid includes, without limitation, reoviral nucleic acid that is essentially free of non-reoviral (e.g., host cell) nucleic acid, or a reoviral genomic segment that is essentially free of nucleic acid corresponding to other genomic segments. In addition, an isolated nucleic acid can include an engineered nucleic acid such as a recombinant or synthetic nucleic acid.

A mutant reovirus as described herein can be generated by reconstituting genome segments containing at least a mutation or modification using methods known in the art. See, for example, Schiff et al., "Orthoreoviruses and Their Replication," Ch 52, in *Fields Virology*, Knipe and Howley, eds., 2006, Lippincott Williams and Wilkins; Smith et al., 1969, *Virology* 39(4):791-810; and U.S. Pat. Nos. 7,186,542; 7,049, 127; 6,808,916; and 6,528,305. A mutant reovirus also can be generated by expressing the reovirus genome segments using a plasmid-based reverse genetic system to produce an ISVP. See, for example, Kobayashi et al., 2007, *Cell Host and Microbe* 1:147-57. As used herein, a genetically-engineered or mutant ISVP is a mutant reovirus and refers to an ISVP generated from a reovirus carrying a genetically-engineered or a spontaneously generated mutation affecting at least the sigma3 polypeptide. The ISVPs described herein are stable and can be propagated as ISVPs for multiple (e.g., more than one, e.g., 2, 3, 4, 5, 10, 20, 50, or more) passages.

The mutant reoviruses described herein, produced via a genetically-engineered ISVP or via a plasmid-based reverse genetic system, can be cultured in, for example, human neoplastic cells or L929 mouse fibroblast cells. Mutant reoviruses disclosed herein can be cultured in cells that are only permissive to reovirus strains lacking the sigma3 polypeptide. Using such cell lines to passage the mutant reoviruses described herein can allow for selection of the mutants and also can be used to reduce or prevent reversions of the mutation(s).

The mutant reoviruses described herein, optionally, exhibit increased infectivity and/or decreased immunogenicity as compared to a non-mutant reovirus (e.g., a control reovirus) and can be selected on the basis of such traits. Increased infectivity can be evidenced by an increase in the range of neoplastic cells and/or the number of cells that are infected by a mutant reovirus compared to a reovirus that expresses a functional sigma3 polypeptide (e.g., an intact virion; e.g., a wild type reovirus). Decreased immunogenicity of mutant reoviruses can be evidenced by the inability of such mutant reoviruses to induce a significant immune response in the subject. The mutant reoviruses described herein also can be screened and selected for other desirable traits including, but not limited to, a faster rate of replication; a faster rate of packaging; the ability to induce apoptosis; the ability to affect lysis in and effectively kill human neoplastic cells lines; the ability to release effective tumor epitopes; interaction with standard chemotherapies; and an increased number of viral progeny. Additionally, mutant reoviruses can be selected for the ability to lytically infect a neoplastic cell (e.g., a mammalian cell having an active Ras pathway). See, for example, U.S. Pat. No. 7,052,832.

The reovirus is optionally a reovirus modified to reduce or eliminate an immune reaction to the reovirus. Such a modified reovirus is referred to herein as an immunoprotected reovirus. Such modifications include, but are not limited to, packaging of the reovirus in a liposome, a micelle, or other vehicle to mask the reovirus from the immune system. Alternatively, the outer capsid of the reovirus virion particle may be removed since the proteins present in the outer capsid are the major determinant of the host humoral and cellular responses.

Reoviruses can be purified using standard methodology. See, for example, Schiff et al., "Orthoreoviruses and Their Replication," Ch 52, in *Fields Virology*, Knipe and Howley, eds., 2006, Lippincott Williams and Wilkins; Smith et al., 1969, *Virology* 39(4):791-810; and U.S. Pat. Nos. 7,186,542; 7,049,127; 6,808,916; and 6,528,305. As used herein, purified mutant reoviruses refer to reoviruses that have been separated from cellular components that naturally accompany them. Typically, reoviruses are considered purified when they are at least 70% (e.g., at least 75%, 80%, 85%, 90%, 95%, or 99%) by dry weight, free from the proteins and other cellular components with which they are naturally associated.

The herein provided reoviruses and agents can be administered in vitro or in vivo in a pharmaceutically acceptable carrier. Thus, pharmaceutical compositions that include a reovirus and/or agent that inhibits pro-inflammatory cytokines as described herein are provided. See, for example, U.S. Pat. No. 6,576,234 regarding reoviruses. In addition to one or more reoviruses and/or agents that inhibit pro-inflammatory cytokines, a pharmaceutical composition typically includes a pharmaceutically acceptable carrier. A pharmaceutically acceptable carrier can be a solid, semi-solid, or liquid material that can act as a vehicle, carrier or medium for the reovirus. Thus, compositions containing a reovirus and/or the provided agents can be in the form of tablets, pills, powders, lozenges, sachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Optionally, the compositions containing a reovirus are suitable for infusion. For intravenous infusions, there are two types of fluids that are commonly used, crystalloids and colloids. Crystalloids are aqueous solutions of mineral salts or other water-soluble molecules. Colloids contain larger insoluble molecules, such as gelatin; blood itself is a colloid. The most commonly used crystalloid fluid is normal saline, a solution of sodium chloride at 0.9% concentration, which is close to the concentration in the blood (isotonic). Ringer's lactate or Ringer's acetate is another isotonic solution often used for large-volume fluid replacement. A solution of 5% dextrose in water, sometimes called D5W, is often used instead if the patient is at risk for having low blood sugar or high sodium.

Some examples of suitable carriers include phosphate-buffered saline or another physiologically acceptable buffer, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. A pharmaceutical composition additionally can include, without limitation, lubricating agents such as talc, magnesium stearate, and mineral oil; wetting agents; emulsifying and suspending agents; preserving agents such as methyl- and propylhydroxy-benzoates; sweetening agents; and flavoring agents. Pharmaceutical compositions can be formulated to provide quick, sustained or delayed release of a mutant reovirus after administration by employing procedures known in the art. In addition to the representative formulations described below, other suitable formulations for use in a pharmaceutical composition can be found in Remington: The Science and Practice of Pharmacy (21th ed.) ed. David B. Troy, Lippincott Williams & Wilkins, 2005. For preparing solid compositions such as tablets, a mutant reovirus can be mixed with a pharmaceutical carrier to form a solid composition. Optionally, tablets or pills can be coated or otherwise compounded to provide a dosage form affording the advantage of prolonged action. For example, a tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid formulations that include a reovirus and/or other agents for oral administration or for injection generally include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. These liquid or solid compositions may contain suitable pharmaceutically acceptable excipients as described herein. Such compositions can be administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a face mask tent or intermittent positive pressure breathing machine. Solution, suspension, or powder compositions may be administered, orally or nasally, from devices which deliver the formulation in an appropriate manner.

Another formulation that is optionally employed in the methods of the present disclosure includes transdermal delivery devices (e.g., patches). Such transdermal patches may be used to provide continuous or discontinuous infusion of a mutant reovirus as described herein. The construction and use of transdermal patches for the delivery of pharmaceutical agents is well known in the art. See, for example, U.S. Pat. No. 5,023,252. Such patches can be constructed for continuous, pulsatile, or on-demand delivery of mutant reoviruses.

As described above, reoviruses and/or other agents are, if necessary, coated in a liposome or micelle to reduce or prevent an immune response in a mammal that has developed immunity toward a reovirus. Such compositions are referred to as immunoprotected reoviruses and/or agents. See, for example, U.S. Pat. Nos. 6,565,831 and 7,014,847. In addition, a mutant reovirus as disclosed herein (e.g., one that lacks or is deficient in sigma3 polypeptide or function) can be proteolytically treated with an enzyme to remove or partially remove any of the other outer capsid proteins present.

In the provided methods, the reovirus is administered in a manner so that it can ultimately contact the target tumor or tumor cells, for example, systemically. The route by which the reovirus is administered, as well as the formulation, carrier or vehicle, depends on the location as well as the type of the target cells. A wide variety of administration routes can be employed. For example, for a solid tumor that is accessible, the reovirus can be administered by injection directly to the tumor. For a hematopoietic tumor, for example, the reovirus can be administered intravenously or intravascularly. For tumors that are not easily accessible within the body, such as metastases, the reovirus is administered in a manner such that it can be transported systemically through the body of the mammal and thereby reach the tumor (e.g., intravenously or intramuscularly). Alternatively, the reovirus can be administered directly to a single solid tumor, where it then is carried systemically through the body to metastases. The reovirus can also be administered subcutaneously, intraperitoneally, intrathecally (e.g., for brain tumor), topically (e.g., for melanoma), orally (e.g., for oral or esophageal cancer), rectally (e.g., for colorectal cancer), vaginally (e.g., for cervical or vaginal cancer), nasally, by inhalation spray or by aerosol formulation (e.g., for lung cancer).

Optionally, the virus is administered continuously to a subject at least once per day or up to throughout the day on consecutive days, for a period of time. Thus, the virus is administered, for example, to subjects by means of intravenous administration in any pharmacologically acceptable solution, or as an infusion over a period of time. For example, the substance may be administered systemically by injection (e.g., IM or subcutaneously) or taken orally daily at least once per day, or administered by infusion in a manner that results in the daily delivery into the tissue or blood stream of the subject. When the virus is administered by infusion over a period of time, the period of time is, for example, 1, 2, 3, 4, 5, 6, 7, 8, 9, 10, 12, or 24 hours, or any time between 1 and 24 hours, inclusive, or more. Optionally, the period of time is 5, 15, 30, 60, 90, 120, 150 or 180 minutes, or any time between 5 and 180 minutes, inclusive, or more. Thus, for example, the virus is administered by infusion for 60 minutes or about 60 minutes. Administrations can be repeated daily for 2, 3, 4, 5, 6, 7, 8, 9, 10, 14, 21, 28 days or any number of days between 2 and 28 days, inclusive, or longer.

Therapeutic agents, such as the agents that inhibit production of pro-inflammatory cytokines, of the provided methods are also administered via a wide variety of administration routes. Thus, the agents are administered via any of several routes of administration, including, topically, orally, parenterally, intravenously, intraperitoneally, intramuscularly, subcutaneously, intracavity, transdermally, intrahepatically, intracranially, nebulization/inhalation, or by instillation via bronchoscopy. Optionally, the therapeutic agents are administered continuously in the manner set forth in the description above with respect to oncolytic viruses. Thus, for example, the agent is administered, for example, to subjects by means of intravenous administration in any pharmacologically acceptable solution, or as an infusion over a period of time. Optionally, the agents are administered locally at or near the site of the tumor. Alternatively, the agents are administered systemically. The agents that inhibit pro-inflammatory cytokines are administered in an amount sufficient (i.e., an effective amount) to inhibit one or more pro-inflammatory cytokines. By way of example, effective amounts of platinum compounds include from about 5 to 1000 mg/m² of tumor volume, or any amount in between 5 and 1000 mg/m², inclusive, or more. Thus, for example effective amounts of cisplatin include from about 175-200 mg/m² and effective mounts for carboplatin include from about 100-600 mg/m². Effective amounts of other agents range from 0.001-10,000 mg/kg body weight or any amount in between 0.001 and 10,000 mg/kg body weight, inclusive. Optionally, effective amounts of platinum compounds include approximately 2 to 7 mg/mL minute (AUC) as calculated by the Calvert formula. Optionally, effective amounts of platinum compounds include approximately 5 or 6 mg/mL minute (AUC) as calculated by the Calvert formula. Optionally, the platinum compounds are administered as an intravenous infusion over a period of 30 minutes.

The reovirus is administered in an amount that is sufficient to treat the proliferative disorder (e.g., an effective amount). A proliferative disorder is treated when administration of a reovirus to proliferating cells affects lysis (e.g., oncolysis) of the affected cells, resulting in a reduction in the number of abnormally proliferating cells, a reduction in the size of a neoplasm, and/or a reduction in or elimination of symptoms (e.g., pain) associated with the proliferating disorder. As used herein, the term oncolysis means at least 10% of the proliferating cells are lysed (e.g., at least about 20%, 30%, 40%, 50%, or 75% of the cells are lysed). The percentage of lysis can be determined, for example, by measuring the reduction in the size of a neoplasm or in the number of proliferating cells in a mammal, or by measuring the amount of lysis of cells in vitro (e.g., from a biopsy of the proliferating cells). An effective amount of a virus will be determined on an individual basis and may be based, at least in part, on the particular virus used; the individual's size, age, gender; and the size and other characteristics of the abnormally, proliferating cells. For example, for treatment of a human, approximately $10^3$ to $10^{12}$ plaque forming units (PFU) of a virus are used, depending on the type, size and number of proliferating cells or neoplasms present. The effective amount can be, for example, from about 1.0 PFU/kg body weight to about $10^{15}$ PFU/kg body weight (e.g., from about $10^2$ PFU/kg body weight to about $10^{13}$ PFU/kg body weight). Optionally, the effective amount is about $1\times10^8$ to about $1\times10^{12}$ TCID$_{50}$. Optionally, the effective amount is about $1\times10^{10}$ TCID$_{50}$.

By way of example, 5-6 mg/ml minute (AUC as calculated by the Calvert formula) of an agent that inhibits pro-inflammatory cytokines, such as carboplatin, is administered to the subject and $1\times10^{10}$ TCID$_{50}$ to $3\times10^{10}$ TCID$_{50}$ of a reovirus is administered to the subject. Optionally, the agent that inhibits pro-inflammatory cytokines is administered as a thirty minute to one hour intravenous infusion. Optionally, the reovirus is administered as a one hour intravenous infusion.

Optimal dosages of viruses and therapeutic agents and compositions comprising viruses and agents depend on a variety of factors. The exact amount required will vary from subject to subject, depending on the species, age, weight and general condition of the subject, the severity of the disease being treated, the particular virus or vector used and its mode of administration. Thus, it is not possible to specify an exact amount for every composition. However, an appropriate amount can be determined by one of ordinary skill in the art using only routine experimentation given the guidance provided herein.

Effective dosages and schedules for administering the compositions may be determined empirically. For example, animal models for a variety of proliferative disorders can be obtained from The Jackson Laboratory, 600 Main Street, Bar Harbor, Me. 04609 USA. Both direct (e.g., histology of tumors) and functional measurements (e.g., survival of a subject or size of a tumor) can be used to monitor response to therapies. These methods involve the sacrifice of representative animals to evaluate the population, increasing the animal numbers necessary for the experiments. Measurement of luciferase activity in the tumor provides an alternative method to evaluate tumor volume without animal sacrifice and allowing longitudinal population-based analysis of therapy.

The dosage ranges for the administration of compositions are those large enough to produce the desired effect in which the symptoms of the disease are affected. The dosage should not be so large as to cause adverse side effects, such as unwanted cross-reactions and anaphylactic reactions. The dosage can be adjusted by the individual physician in the event of any counterindications.

Dosages vary and are administered in one or more dose administrations daily, for one or several days. The provided viruses and therapeutic agents are administered in a single dose or in multiple doses (e.g., two, three, four, six, or more doses). For example, where the administration is by infusion, the infusion can be a single sustained dose or can be delivered by multiple infusions. Treatment may last from several days to several months or until diminution of the disease is achieved.

Combinations of the provided viruses and therapeutic agents are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents. By way of example, the agent that inhibits proinflammatory cytokines is administered prior to or at the same time as the oncolytic virus. When one compound is administered prior to another compound, the first compound is administered minutes, hours, days, or weeks prior to administration of the second compound. For example, the first compound can be administered at 1, 2, 3, 4, 5, 6, 7, 8, 9, 10, 12, 24, 36, 48, 60, or 72 hours, or any time between 1 and 72 hours, inclusive, prior to administration of a second compound. Optionally, the first compound is administered more than 72 hours prior to the second compound. By way of another example, the first compound can be administered at 1, 5, 15, 30, 60, 90, or 120 minutes, or any time between 1 and 120 minutes, inclusive, prior to administration of a second compound. Optionally, the first compound is administered at 1, 2, 3, 4, 5, 6, 7, 14, 21, or 28 days, or any amount in between 1 and 28, inclusive, days prior to administration of the second compound. Optionally, the first compound is administered more than 28 days prior to the second compound. For example, the agent that inhibits proinflammatory cytokines is administered from about 1 to 8 hours prior to administration of the oncolytic virus. By way of another example, the agent that inhibits pro-inflammatory cytokines is administered at a time of about one hour prior to administration of the oncolytic virus.

By way of example, one cycle of treatment includes administering the agent that inhibits proinflammatory cytokines and the oncolytic virus includes on day 1. On days 2, 3, 4 and 5, only the oncolytic virus is administered to the subject. Optionally, the subject receives multiple cycles of treatment, for example, two, three, four, five or more cycles of treatment.

Reoviruses or a pharmaceutical composition comprising such reoviruses are optionally packaged into a kit. The kit also includes one or more agents or pharmaceutical compositions comprising such agents that inhibit pro-inflammatory cytokines. It is contemplated that a kit, optionally, also includes one or more chemotherapeutic agents, one or more immunosuppressive agents, and/or one or more anti-antireovirus antibodies. A pharmaceutical composition can be formulated in a unit dosage form. The term "unit dosage forms" refers to physically discrete units suitable as unitary dosages for human subjects and other mammals, each unit containing a predetermined quantity of a mutant reovirus calculated to produce the desired therapeutic effect in association with a suitable pharmaceutically acceptable carrier.

It is contemplated that the provided methods may be combined with other tumor therapies such as chemotherapy, radiotherapy, surgery, hormone therapy and/or immunotherapy. Thus, the oncolytic virus may be administered in conjunction with surgery or removal of the neoplasm. Therefore, provided herewith are methods for the treatment of a solid neoplasm comprising surgical removal of the neoplasm and administration of an oncolytic virus at or near to the site of the neoplasm.

It is further contemplated that the compositions in the provided methods are, optionally, administered in conjunction with or in addition to known anticancer compounds or chemotherapeutic agents. Chemotherapeutic agents are compounds which may inhibit the growth of tumors. Such agents, include, but are not limited to. 5-fluorouracil, mitomycin C, methotrexate, hydroxyurea, cyclophosphamide, dacarbazine, mitoxantrone, anthracyclins (Epirubicin and Doxurubicin), antibodies to receptors, such as herceptin, etopside, pregnasome, hormone therapies such as tamoxifen and anti-estrogens, interferons, aromatase inhibitors, progestational agents and LHRH analogs.

As used herein the terms treatment, treat, treating or ameliorating refers to a method of reducing the effects of a disease or condition or symptom of the disease or condition. Thus in the disclosed method, treatment can refer to a 10%, 20%, 30%, 40%, 50%, 60%, 70%, 80%, 90% or 100% reduction or amelioration in the severity of an established disease or condition or symptom of the disease or condition. For example, the method for treating cancer is considered to be a treatment if there is a 10% reduction in one or more symptoms of the disease in a subject as compared to control. Thus the reduction can be a 10, 20, 30, 40, 50, 60, 70, 80, 90, 100% or any percent reduction in between 10 and 100 as compared to native or control levels. It is understood that treatment does not necessarily refer to a cure or complete ablation of the disease, condition or symptoms of the disease or condition.

As used herein, references to decreasing, reducing, or inhibiting include a change of 10, 20, 30, 40, 50, 60, 70, 80, 90 percent or greater as compared to a control level. Such terms can include but do not necessarily include complete elimination.

As used herein, the term subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, whether male or female, are intended to be covered. As used herein, patient or subject may be used interchangeably and can refer to a subject with a disease or disorder. The term patient or subject includes human and veterinary subjects.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an inhibitor is disclosed and discussed and a number of modifications that can be made to a number of molecules including the inhibitor are discussed, each and every combination and permutation of the inhibitor, and the modifications that are possible are specifically contemplated unless specifically indicated to the contrary. Likewise, any subset or combination of these is also specifically contemplated and disclosed. This concept applies to all aspects of this disclosure including, but not limited to, steps in methods of using the disclosed compositions. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

EXAMPLES

Example 1

Anti-tumor Activity of Reovirus and Cisplatin in Mouse Melanoma Model

Reovirus type 3 Dearing (RV) has demonstrated oncolytic activity in numerous in vitro systems, in vivo murine models and early clinical trials. To further these studies, the in vitro and in vivo oncolytic activity of RV in combination with cisplatin (CP), a pseudoalkylating chemotherapeutic which causes DNA cross-linking and is active in a wide range of cancers, was examined. The effect of RV and CP was assessed in vitro for synergistic tumor kill and mechanism of tumor death. A synergistic interaction (combination index value (CIV) of less than one) was observed between RV and CP (CIV: ED50, 0.42±0.03; ED75, 0.30±0.02; ED90, 0.24±0.01) on B16.F10 cells. Flow cytometric analysis showed a marked increase in apoptotic cells following combined exposure, compared to single agent exposure.

Figure 1B:
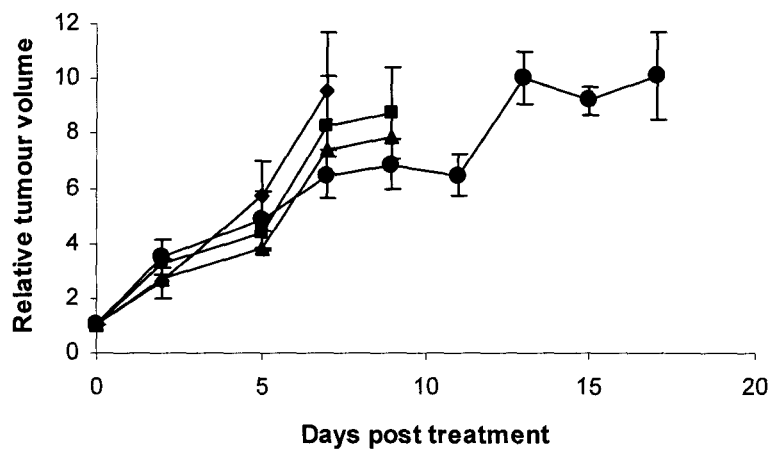
Figure 1C:
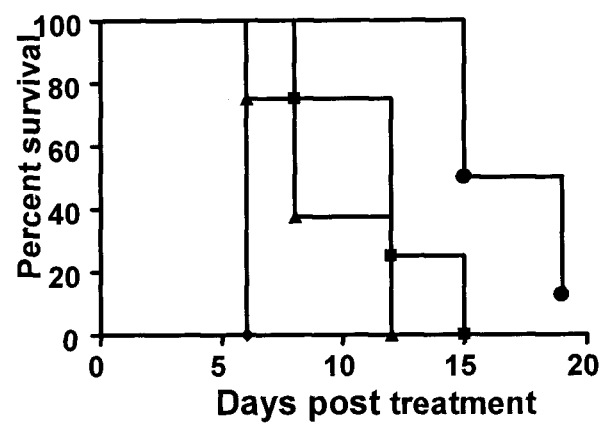
Figure 1D:
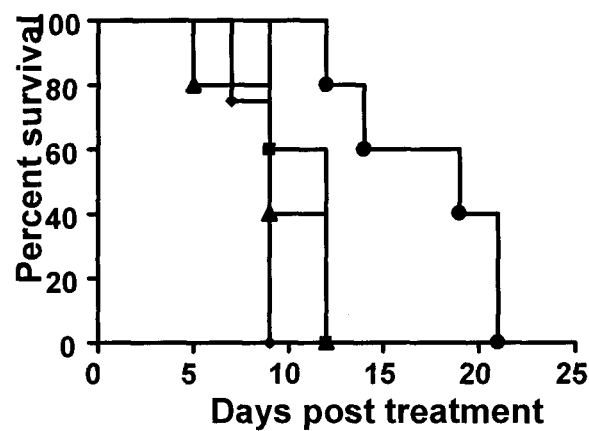
Figure 2:
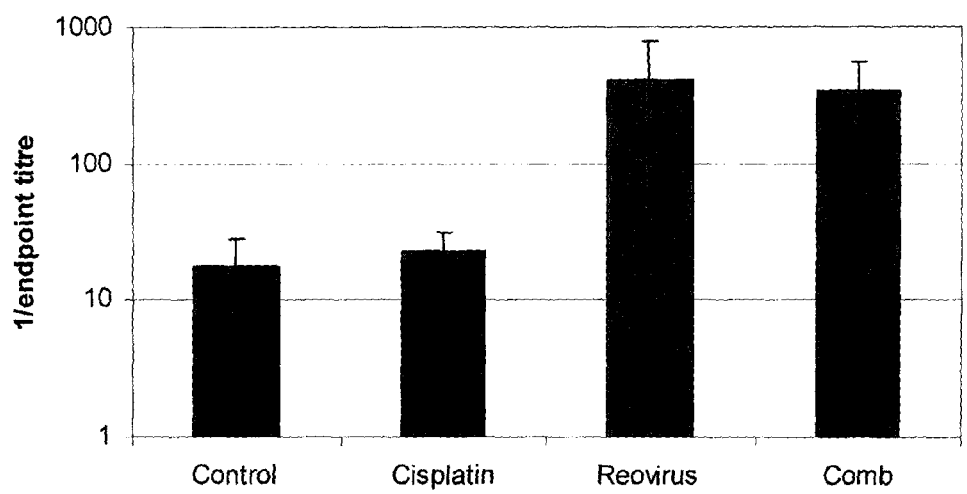
FIG. 2 is a graph showing the neutralizing anti-reovirus antibody (NARA) response after no treatment (control) or treatment with reovirus, cisplatin or the combination of reovirus and cisplatin.
Figure 3A:
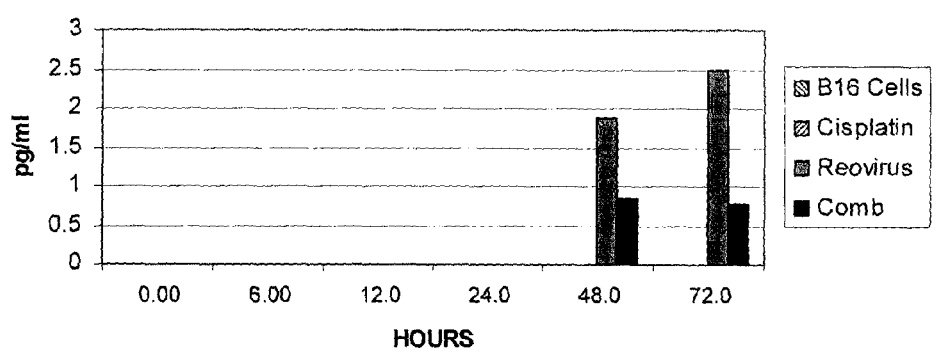
FIGS. 3A, 3B, 3C, 3D, 3E, 3F, and 3G are graphs showing pro-inflammatory cytokine response is abrogated by cisplatin. The response of IL-1I (FIG. 3A), IL-3 (FIG. 3B), IL-6 (FIG. 3C), IL-12 (FIG. 3D), IL-17 (FIG. 3E), MIP-1I (FIG. 3F) and RANTES (FIG. 3G) were measured after no treatment (control) or treatment with reovirus, cisplatin or the combination of reovirus and cisplatin.
Figure 3B:
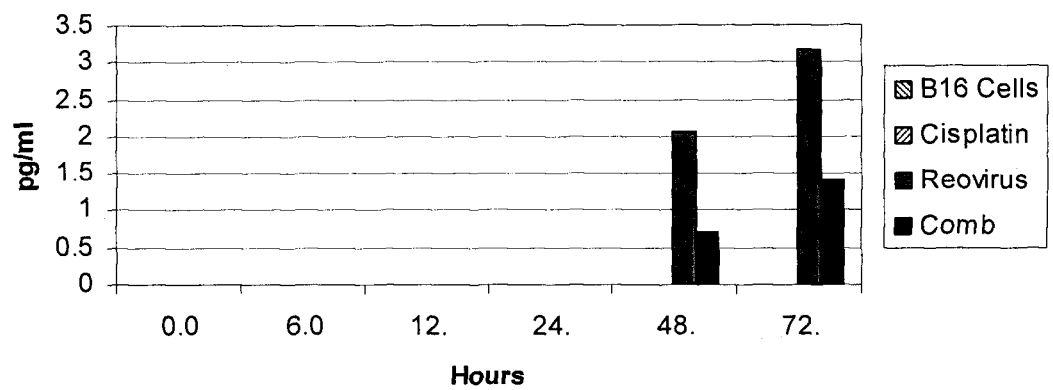
Figure 3C:
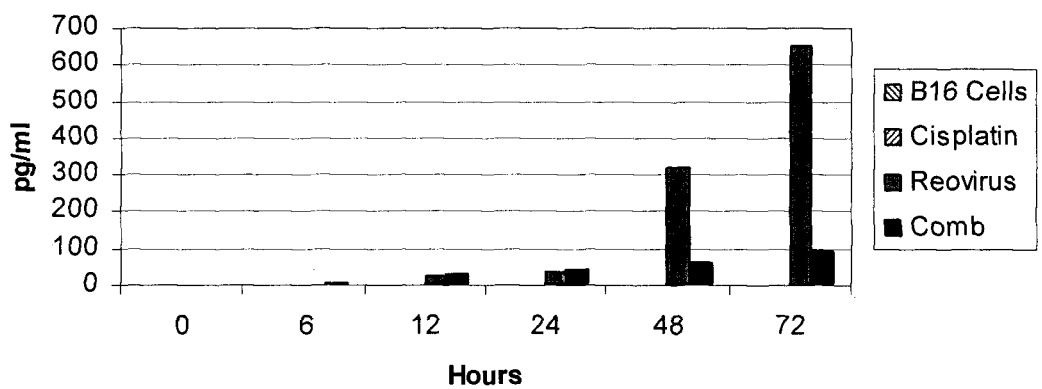
Figure 3D:
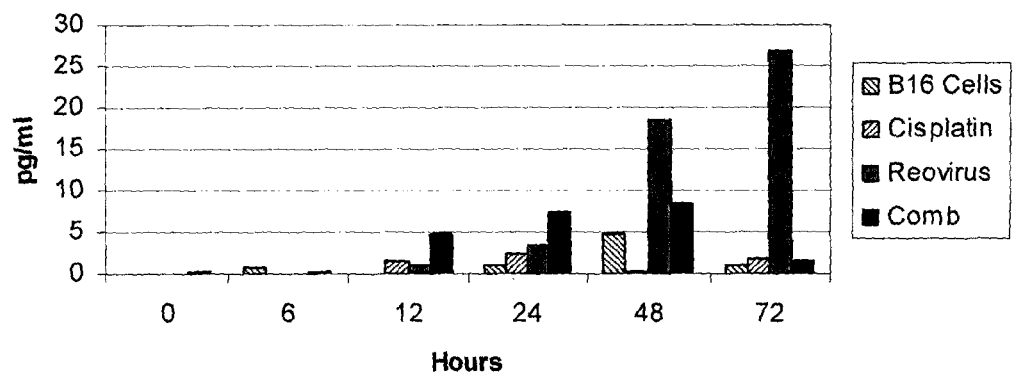
Figure 3E:
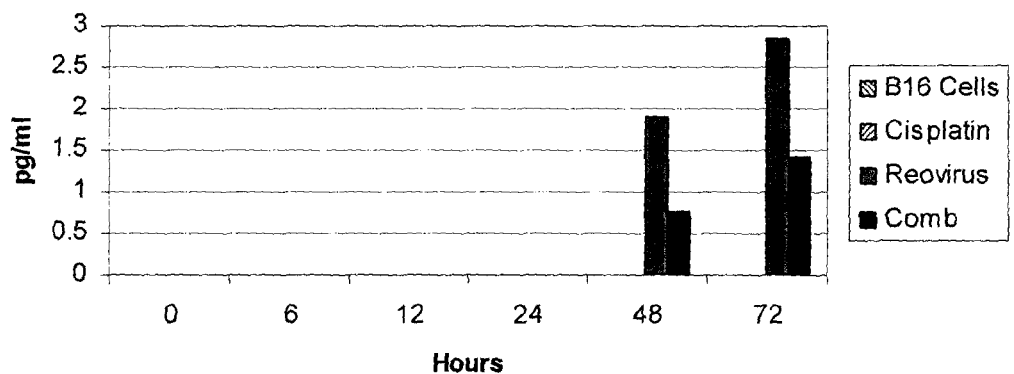
Figure 3F:
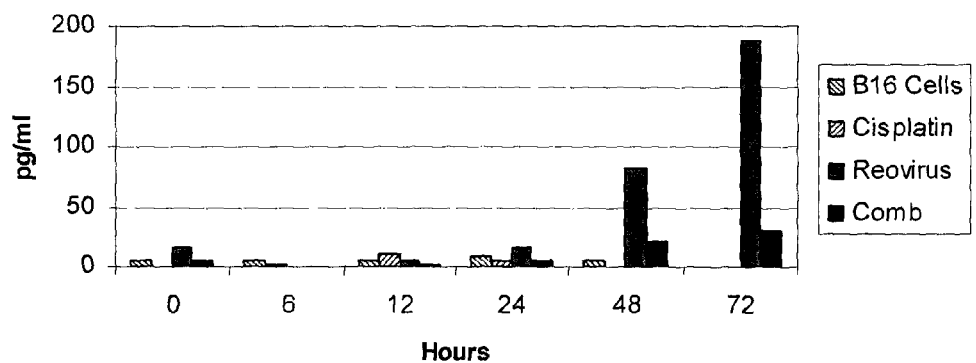
Figure 3G:
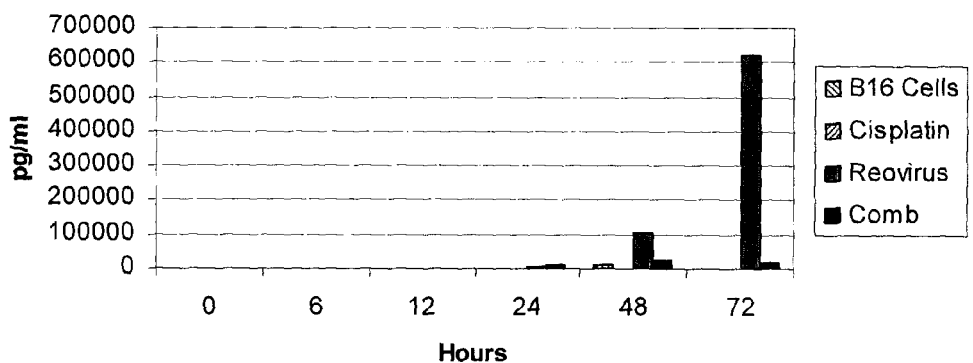

For in vivo evaluation, subcutaneous B16.F10 tumors in C57Bl/6 mice or K1735 tumors in C3H mice were treated with intratumoral (i.t.) RV and intraperitoneal (i.p.) CP either alone or in combination. Tumor volume was estimated thrice weekly. Tumors and organs were harvested post-treatment for viral retrieval and histology; serum samples were tested for cytokine production and induction of neutralising anti-reovirus antibody (NARA). FIGS. 1A, 1B, 1C and 1D show reduced tumor growth and increased survival following reovirus/cisplatin combination therapy. C57Bl/6 (FIGS. 1A and 1C) and C3H (FIGS. 1B and 1D) mice bearing subcutaneous B16.F10 and K1735 tumors respectively were treated on days 1 and 4 with either reovirus alone i.t. (squares), cisplatin alone i.p. (triangles), or reovirus and cisplatin in combination (circles). Control treated mice (diamonds) received PBS. Tumors were measured on the days indicated and tumor volume expressed as tumor volume relative to volume at commencement of treatment (FIGS. 1A and 1B). Mice were euthanized when tumors exceeded 15 mm in any one dimension. Survival is expressed as Kaplan-Myer plots (FIGS. 1C and 1D). These data show reduced tumor growth and extended median survival time was observed in mice treated with RV/CP combination therapy compare to single agent treatments (FIGS. 1A, 1B, 1C and 1D). Mean relative tumor volumes ±SD at day 12 were, control: all reached endpoint, RV alone: 8.92±6.94, CP alone: 9.87±2.80, RV plus CP: 3.86±2.24. Median survival (days) were, control: 6, RV: 12, CP: 8, combination of RV and CP: 17. Live virus was recovered from the tumors of all RV only treated animals and from the liver and heart of ⅙ mice. In contrast live virus was detected in only 50% of tumors from combination treated mice but in the liver of 4/6 mice. CP did not affect the neutralizing anti-reovirus antibody (NARA) response to RV (FIG. 2), but caused a marked attenuation of production of proinflammatory cytokines to RV when used in combination (FIGS. 3A, 3B, 3C, 3D, 3E, 3F, and 3G).

Taken together, these results show that the addition of chemotherapeutic agents can significantly enhance the anti-tumor efficacy of RV therapy. Furthermore, a reduction in viral inflammatory responses in vital organs by concomitant chemotherapy may allow more intensive dosing schedules to increase overall efficacy of the reovirus.

Example 2

Reovirus and Carboplatin Protocols for Humans

This is a study design of reovirus given intravenously with carboplatin every 3 weeks.

Carboplatin is administered as a 30 minute intravenous infusion at a dose calculated by the Calvert formula (AUC 5 mg/mL minute or 6 mg/mL minute with GFR measured by 51Cr EDTA). Reovirus is then administered as a 1 hour intravenous infusion at a dose of $1\times10^{10}$ or $3\times10^{10}$ $TCID_{50}$.

On days 2 through 5, only reovirus will be administered, using the same dose and method as used on Day 1.

TABLE 2

Dosing Methods

|  | Carboplatin Dose AUC mg/mL min Day 1 only | Reovirus dose ($TCID_{50}$) Days 1-5 |
|---|---|---|
| Method 1 | 5 | $1 \times 10^{10}$ |
| Method 2 | 5 | $3 \times 10^{10}$ |
| Method 3 | 6 | $1 \times 10^{10}$ |
| Method 4 | 6 | $3 \times 10^{10}$ |

What is claimed is:

1. A method for treating a proliferative disorder in a subject, comprising the steps of:
   (a) administering to the subject one or more reoviruses having IDAC Accession No. 190907-01; and
   (b) administering to the subject one or more agents that inhibit expression or activity of a pro-inflammatory cytokine but does not inhibit production of neutralizing anti-reovirus antibodies (NARA).

2. The method of claim 1, wherein approximately $10^3$ to $10^{12}$ plaque forming units (PFU) of the oncolytic virus is administered to the subject.

3. The method of claim 2, wherein approximately $10^8$ to $10^{12}$ plaque forming units (PFU) of the oncolytic virus is administered to the subject.

4. The method of claim 1, wherein approximately $10^8$ to $10^{12}$ TCID$_{50}$ of the oncolytic virus is administered to the subject.

5. The method of claim 1, wherein approximately 5 to 1000 mg/m$^2$ of the agent that inhibits proinflammatory cytokines is administered to the subject.

6. The method of claim 1, wherein approximately 0.001-10,000 mg/kg body weight of the agent that inhibits proinflammatory cytokinesis administered to the subject.

7. The method of claim 1, wherein 2 to 7 mg/mL minute (AUC) of the agent that inhibits proinflammatory cytokines is administered to the subject.

8. The method of claim 1, wherein the agent is a platinum compound.

9. The method of claim 8, wherein the platinum compound is selected from the group consisting of cisplatin, carboplatin and oxaliplatin.

10. The method of claim 9, wherein approximately 175-200 mg/m$^2$ of the cisplatin is administered to the subject.

11. The method of claim 9, wherein approximately 200-600 mg/m$^2$ of the carboplatin is administered to the subject.

12. The method of claim 9, wherein 5 or 6 mg/mL minute (AUC) of the carboplatin is administered to the subject.

13. The method of claim 1, wherein the agent that inhibits proinflammatory cytokines is administered at the same time, before or after the reovirus.

14. The method of claim 13, wherein the agent that inhibits pro-inflammatory cytokines is administered at the same time as the reovirus.

15. The method of claim 13, wherein the agent that inhibits pro-inflammatory cytokines is administered before the reovirus.

16. The method of claim 15, wherein the agent is administered from 1 to 12 hours before the oncolytic virus.

17. The method of claim 15, wherein the agent is administered from 1 to 60 minutes before the oncolytic virus.

18. The method of claim 1, wherein the reovirus is administered in multiple doses.

19. The method of claim 18, wherein the agent that inhibits pro-inflammatory cytokines is administered once.

20. The method of claim 18, wherein the agent that inhibits pro-inflammatory cytokines is administered in multiple doses.

* * * * *

SEQUENCE LISTING

<160> NUMBER OF SEQ ID NOS: 21

<210> SEQ ID NO 1
<211> LENGTH: 1416
<212> TYPE: DNA

<213> ORGANISM: Reovirus

<400> SEQUENCE: 1

```
gctattggtc ggatggatcc tcgcctacgt gaagaagtag tacggctgat aatcgcatta      60
acgagtgata atggagcatc actgtcaaaa gggcttgaat caagggtctc ggcgctcgag     120
aagacgtctc aaatacactc tgatactatc ctccggatca cccagggact cgatgatgca     180
aacaaacgaa tcatcgctct tgagcaaagt cgggatgact tggttgcatc agtcagtgat     240
gctcaacttg caatctccag attggaaagc tctatcggag ccctccaaac agttgtcaat     300
ggacttgatt cgagtgttac ccagttgggt gctcgagtgg acaacttga dacaggactt     360
gcagagctac gcgttgatca cgacaatctc gttgcgagag tggatactgc agaacgtaac     420
attggatcat tgaccactga gctatcaact ctgacgttac gagtaacatc catacaagcg     480
gatttcgaat ctaggatatc cacgttagag cgcacggcgg tcactagcgc gggagctccc     540
ctctcaatcc gtaataaccg tatgaccatg ggattaaatg atggactcac gttgtcaggg     600
aataatctcg ccatccgatt gccaggaaat acgggtctga atattcaaaa tggtggactt     660
cagtttcgat ttaatactga tcaattccag atagttaata ataacttgac tctcaagacg     720
actgtgtttg attctatcaa ctcaaggata ggcgcaactg agcaaagtta cgtggcgtcg     780
gcagtgactc ccttgagatt aaacagtagc acgaaggtgc tggatatgct aatagacagt     840
tcaacacttg aaattaattc tagtggacag ctaactgtta gatcgacatc cccgaatttg     900
aggtatccga tagctgatgt tagcggcggt atcggaatga gtccaaatta taggtttagg     960
cagagcatgt ggataggaat tgtctcctat tctggtagtg ggctgaattg gagggtacag    1020
gtgaactccg acatttttat tgtagatgat tacatacata tatgtcttcc agcttttgac    1080
ggtttctcta tagctgacgg tggagatcta tcgttgaact ttgttaccgg attgttacca    1140
ccgttactta caggagacac tgagcccgct tttcataatg acgtggtcac atatggagca    1200
cagactgtag ctatagggtt gtcgtcgggt ggtgcgcctc agtatatgag taagaatctg    1260
tgggtggagc agtggcagga tggagtactt cggttacgtg ttgaggggg tggctcaatt    1320
acgcactcaa acagtaagtg gcctgccatg accgtttcgt acccgcgtag tttcacgtga    1380
ggatcagacc accccgcggc actggggcat ttcatc                              1416
```

<210> SEQ ID NO 2
<211> LENGTH: 1331
<212> TYPE: DNA
<213> ORGANISM: Reovirus

<400> SEQUENCE: 2

```
gctattcgct ggtcagttat ggctcgcgct gcgttcctat tcaagactgt tgggtttggt      60
ggtctgcaaa atgtgccaat taacgacgaa ctatcttcac atctactccg agctggtaat     120
tcaccatggc agtaacacag ttttttagac tggataagcc ttgggagggg tttagctaca     180
tcggctctcg ttccgacggc tgggtcaaga tactatcaaa tgagttgcct tctaagtggc     240
actctccaga ttccgttccg tcctaaccac cgatggggag acattaggtt cttacgctta     300
gtgtggtcag ctcctactct cgatggatta gtcgtagctc caccacaagt tttggctcag     360
cccgctttgc aagcacaggc agatcgagtg tacgactgcg atgattatcc atttctagcg     420
cgtgatccaa gattcaaaca tcgggtgtat cagcaattga gtgctgtaac tctacttaac     480
ttgacaggtt ttggcccgat ttcctacgtt cgagtggatg aagatatgtg gagtggagat     540
gtgaaccagc ttctcatgaa ctatttcggg cacacgtttg cagagattgc atacacattg     600
```

```
tgtcaagcct cggctaatag gccttgggaa tatgacggta catatgctag gatgactcag     660
attgtgttat ccttgttctg ctatcgtat gtcggtgtaa ttcatcagca gaatacgtat      720
cggacattct attttcagtg taatcggcga ggtgacgccg ctgaggtgtg gattctttct    780
tgttcgttga accattccgc acaaattaga ccgggtaatc gtagcttatt cgttatgcca    840
actagcccag attggaacat ggacgtcaat ttgatcctga gttcaacgtt gacggggtgt    900
ttgtgttcgg gttcacagct gccactgatt gacaataatt cagtacctgc agtgtcgcgt    960
aacatccatg gctggactgg tagagctggt aaccaattgc atgggttcca ggtgagacga   1020
atggtgactg aattttgtga caggttgaga cgcgatggtg tcatgaccca agctcagcag   1080
aatcaagttg aagcgttggc agatcagact caacagttta agagggacaa gctcgaaacg   1140
tgggcgagag aagacgatca atataatcag gctcatccca actccacaat gttccgtacg   1200
aaaccattta cgaatgcgca atggggacga ggtaatacgg gggcgactag tgccgcgatt   1260
gcagccctta tctgatcgtc ttggagtgag ggggtccccc cacacacctc acgactgacc   1320
acacattcat c                                                          1331
```

<210> SEQ ID NO 3
<211> LENGTH: 1198
<212> TYPE: DNA
<213> ORGANISM: Reovirus

<400> SEQUENCE: 3

```
gctaaagtca cgcctgtcgt cgtcactatg gcttcctcac tcagagctgc gatctccaag      60
atcaagaggg atgacgtcgg tcagcaagtt tgtcctaatt atgtcatgct gcggtcctct    120
gtcacaacaa aggtggtacg aaatgtggtt gagtatcaaa ttcgtacggg cggattcttt    180
tcgtgcttag ctatgctaag gccactccag tacgctaagc gtgagcgttt gcttggtcag    240
aggaatctgg aacgtatatc gactagggat atccttcaga ctcgtgattt acactcacta    300
tgtatgccaa ctcctgatgc gccaatgtct aatcatcaag catccaccat gagagagctg    360
atttgcagtt acttcaaggt cgatcatgcg gatgggttga aatatatacc catggatgag    420
agatactctc cgtcatcact tgccagattg tttaccatgg gcatggctgg gctgcacatt    480
accactgagc catcttataa gcgtgttccg attatgcact tagctgcgga cttggactgt    540
atgacgctgc tctaccttta catgattacg cttgatggtg atactgtggt tcctgtcgct    600
ccaacactgt cagcggaaca gcttctggac gacggactca aaggattagc atgcatggat    660
atctcctatg gatgtgaggt ggacgcgaat agccggccgg ctggtgatca gagtatggac    720
tcttcacgct gcatcaacga gttgtattgc gaggagacag cagaagccat ctgtgtgctt    780
aagacatgcc ttgtgttaaa ttgcatgcag tttaaacttg agatggatga cctagcacat    840
aacgctgctg agctggacaa gatacagatg atgataccct tcagtgagcg tgttttttagg   900
atggcctcgt cctttgcgac tattgatgcc cagtgtttta ggttttgcgt gatgatgaag   960
gataaaaatc tgaaaataga tatgcgtgaa acgacgagac tgtggactcg ttcagcatca  1020
gatgattctg tggccacgtc atctttaagt atttccctgg accggggtcg atgggtggcg  1080
gctgacgcca gtgatgctag actgctggtt tttccgattc gcgtgtaatg ggtgagtgag  1140
ctgatgtggt cgccaagaca tgtgccggtg tcttggtggt gggtgacgcc taatcatc    1198
```

<210> SEQ ID NO 4
<211> LENGTH: 1196
<212> TYPE: DNA
<213> ORGANISM: Reovirus

```
<400> SEQUENCE: 4 gctattttg cctcttccca gacgttgtcg caatggaggt gtgcttgccc aacggtcatc     60
aggtcgtgga cttaattaac aacgcttttg aaggtcgtgt atcaatctac agcgcgcaag   120
agggatggga caaaacaatc tcagcacagc cagatatgat ggtatgtggt ggcgccgtcg   180
tttgcatgca ttgtctaggt gttgttggat ctctacaacg caagctgaag catttgcctc   240
accatagatg taatcaacag atccgtcatc aggattacga cgatgtacag ttcgcagacc   300
gtgttactgc tcactggaag cggggtatgc tgtccttcgt tgcgcagatg cacgagatga   360
tgaatgacgt gtcgccagat gacctggatc gtgtgcgtac tgagggaggt tcactagtgg   420
agctgaaccg gcttcaggtt gacccaaatt caatgtttag atcaatacac tcaagttgga   480
cagatccttt gcaggtggtg gacgaccttg acactaagct ggatcagtac tggacagcct   540
taaacctgat gatcgactca tccgacttga tacccaactt tatgatgaga gacccatcac   600
acgcgttcaa tggtgtgaaa ctgaagggag atgctcgtca aacccaattc tccaggactt   660
ttgattcgag atcgagtttg aatgggggtg tgatggttta tgattactct gagctggatc   720
atgatccatc gaagggccgt gcttacagaa aggaattggt gacgccagct cgagatttcg   780
gtcactttgg attatcccat tattctaggg cgactacccc aatccttgga agatgccgg    840 ccgtattctc aggaatgttg actgggaact gtaaaatgta tccattcatt aaaggaacgg   900
ctaagctgaa gacagtgcgc aagctagtgg aggcagtcaa tcatgcttgg ggtgtcgaga   960
agattagata tgctcttggg ccaggtggca tgacgggatg gtacaatagg actatgcaac  1020
aggcccccat tgtgctaact cctgctgctc tcacaatgtt cccagatacc atcaagtttg  1080
gggatttgaa ttatccagtg atgattggcg atccgatgat tcttggctaa acaccccat   1140 cttcacagcg ccgggcttga ccaacctggt gtgacgtggg acaggcttca ttcatc       1196

<210> SEQ ID NO 5
<211> LENGTH: 2304
<212> TYPE: DNA
<213> ORGANISM: Reovirus

<400> SEQUENCE: 5
gctattcgcg gtcatggctt acatcgcagt tcctgcggtg gtggattcac gttcgagtga    60
ggctattgga ctgctagaat cgtttggagt agacgctggg gctgacgcga atgacgtttc   120
atatcaagat catgactatg tgttggatca gttacagtac atgttagatg gatatgaggc   180
tggtgacgtt atcgatgcac tcgtccacaa gaattggtta catcactctg tctattgctt   240
gttgccaccc aaaagtcaac tattagagta ttggaaaagt aatccttcag cgataccgga   300
caacgttgat cgtcggcttc gtaaacgact aatgctaaag aaagatctca ggaaagatga   360
tgaatacaat cagctagcgc gtgctttcaa gatatcggat gtctacgcac ctctcatctc   420
atccacgacg tcaccgatga caatgataca gaacttgaat cgaggcgaga tcgtgtacac   480
cacgacggac agggtaatag ggctagaat cttgttatat gctcctagaa agtactatgc   540
gtcaactctg tcatttacta tgactaagtg catcattccg tttggtaaag aggtgggtcg   600
tgttcctcac tctcgattta atgttggcac atttccgtca attgctaccc cgaaatgttt   660
tgtcatgagt ggggttgata ttgagtccat cccaaatgaa tttatcaagt tgtttttacca   720 gcgcgtcaag agtgttcacg ctaacatact aaatgacata tctcctcaga tcgtctctga   780
catgataaac agaaagcgtc tgcgcgttca tactccatca gatcgtcgag ccgcgcagtt   840
gatgcatttg ccttaccatg ttaaacgagg agcgtctcac gtcgacgttt acaaggtgga   900
```

-continued

```
tgttgtagac atgttgttcg aggtagtgga tgtggccgat gggttgcgca acgtatctag    960
gaaactaact atgcataccg ttcctgtatg tattcttgaa atgttgggta ttgagattgc   1020
ggactattgc attcgtcaag aggatggaat gctcacagat tggttcctac ttttaaccat   1080
gctatctgat ggcttgactg atagaaggac gcattgtcaa tacttgatta atccgtcaag   1140
tgtgcctcct gatgtgatac ttaacatctc aattactgga tttataaata gacatacaat   1200
cgatgtcatg cctgacatat atgacttcgt taaacccatt ggcgctgtgc tgcctaaggg   1260
atcatttaaa tcaacaatta tgagagttct tgattcaata tcaatattag gaatccaaat   1320
catgccgcgc gcgcatgtag ttgactcaga tgaggtgggc gagcaaatgg agcctacgtt   1380
tgagcaggcg gttatggaga tatacaaagg gattgctggc gttgactcgc tggatgatct   1440
catcaagtgg gtgttgaact cggatctcat tccgcatgat gacaggcttg gtcaattatt   1500
tcaagcgttt ttgcctctcg caaaggactt attagctcca atggccagaa agttttatga   1560
taactcaatg agtgagggta gattgctaac attctctcat gccgacagtg agttgctgaa   1620
cgcaaattat tttggtcatt tattgcgact aaaaatacca tatattacag aggttaatct   1680
gatgattcgc aagaatcgtg agggtggaga gctatttcag cttgtgttat cttatctata   1740
taaaatgtat gctactagcg cgcagcctaa atggtttgga tcattattgc gattgttaat   1800
atgtccctgg ttacatatgg agaaattaat aggagaagca gacccggcat ctacgtcggc   1860
tgaaattggg tggcatatcc ctcgtgaaca gctgatgcaa gatggatggt gtggatgtga   1920
agacggattc attccctatg ttagcatacg tgcgccaaga ctggttatag aggagttgat   1980
ggagaagaac tggggccaat atcatgccca agttattgtc actgatcagc ttgtcgtagg   2040
cgaaccgcgg agggtatctg ctaaggctgt gatcaagggt aaccacttac cagttaagtt   2100
agtttcacga tttgcatgtt tcacattgac ggcgaagtat gagatgaggc tttcgtgcgg   2160
ccatagcact ggacgtggag ctgcatacag tgcgagacta gctttccgat ctgacttggc   2220
gtgatccgtg acatgcgtag tgtgacacct gctcctaggt caatgggggt aggggcggg    2280
ctaagactac gtacgcgctt catc                                           2304
```

<210> SEQ ID NO 6
<211> LENGTH: 2204
<212> TYPE: DNA
<213> ORGANISM: Reovirus

<400> SEQUENCE: 6

```
ggctaatctg ctgaccgtta ctctgcaaag atggggaacg cttcctctat cgttcagacg     60
atcaacgtca ctggagatgg caatgtattt aaaccatcag ctgaaacttc atctaccgct    120
gtaccatcgt taagcttatc acctggaatg ctgaatcccg gaggggtacc atggattgct    180
gttggagatg agacatctgt gacttcacca ggcgcattac gtcgaatgac gtcaaaggac    240
atcccggaca cggcaataat caacacagac aattcatcag cgccgtgcc aagcgaatca    300
gccttggtgc cctacatcga tgagccgctg gtagtggtta cagagcatgc tattaccaac    360
ttcaccaaag ctgagatggc acttgaattc aatcgtgagt tccttgacaa gatgcgtgtg    420
ctgtcagtgt caccaaaata ttcggatctt ctgacctatg ttgactgcta cgtcggtgtg    480
tctgctcgtc aggcttttaaa caattttcag aaacaagtgc ctgtgattac acctactagg    540
cagacgatgt atgtcgactc gatacaagcg gccttgaaag ctttagaaaa gtgggagatt    600
gatctgagag tggctcaaac gttgctgcct acgaacgttc cgattggaga agtctcttgt    660
ccaatgcagt cggtagtgaa actgctggat gatcagctgc cagatgacag cctgatacgg    720
```

```
aggtatccca aggaagccgc cgtcgctttg gctaaacgaa acgggggaat acaatggatg    780
gacgtatcag aaggcaccgt gatgaacgag gctgtcaacg ctgttgcagc tagtgcactg    840
gcaccttcag catcagcccc acccttagaa gagaagtcaa agttaaccga caagcgatg    900
gatctcgtga ccgcggctga gcctgagata attgcctcac tcgcgccagt tcccgcaccc    960
gtgtttgcca taccacctaa accagcagat tataatgtgc gtactctgag gatcgacgag   1020
gccacttggc tgcgaatgat tccaaaatca atgaacacac ttttcaaat ccaggtgact    1080
gataacacag gaactaattg gcatctcaat ttgaggggg ggactcgtgt agtgaatctg    1140
gaccaaatcg ctccgatgcg gtttgtatta gatctagggg gaaagagtta taaagagacg   1200
agctgggatc aaacggcaa gaaggtcgga ttcatcgttt ttcaatcgaa gataccattc    1260
gaactttgga ctgctgcttc acagatcggt caagccacgg tggttaacta tgtccaacta   1320
tacgctgaag acagctcatt taccgcgcag tctatcattg ctactacctc tttggcttat   1380
aactatgagc ctgagcagtt gaataagact gaccctgaga tgaattatta tcttttggcg   1440
acctttatag actcagccgc tataacgcca acgaatatga cacagcctga tgtttgggat   1500
gccttgctga cgatgtcccc actatcagct ggcgaggtga cagtgaaggg tgcggtagtg   1560
agtgaagtag tccctgcaga cttgataggt agctacactc cagaatccct aaacgcctca   1620
cttccgaatg atgctgctag atgcatgatc gatagagctt cgaagatagc cgaagcaatc   1680
aagattgatg atgatgctgg accagatgaa tattccccaa actctgtacc aattcaaggt   1740
cagcttgcta tctcgcaact cgaaactgga tatggtgtgc gaatattcaa ccctaaaggg   1800
atccttttcta aaattgcatc tagggcaatg caggctttca ttggtgaccc gagcacaatc   1860
atcacgcagg cggcgccagt gttatcagac aagaataatt ggattgcatt ggcacaggga   1920
gtgaaaacta gtctgcgtac taaaagtcta tcagcgggag tgaagactgc agtgagtaag   1980
ctgagctcat ctgagtctat ccagaattgg actcaaggat tcttggataa agtgtcagcg   2040
cattttccag caccaaagcc cgattgtccg actagcggag atagtggtga atcgtctaat   2100
cgccgagtga agcgcgactc atacgcagga gtggtcaaac gtgggtacac acgttaggcc   2160
gctcgccctg gtgacgcggg gttaagggat gcaggcaaat catc                    2204

<210> SEQ ID NO 7
<211> LENGTH: 2241
<212> TYPE: DNA
<213> ORGANISM: Reovirus

<400> SEQUENCE: 7
gctaaagtga ccgtggtcat ggcttcattc aagggattct ccgccaacac tgttccagtt     60
tctaaggcca agcgtgacat atcatctctt gccgctactc ctggacttcg ttcacaatcc    120
ttcactccgt ctgtggatat gtctcaatcg cgtgaattcc tcacaaaggc aattgagcaa    180
gggtccatgt ctatacctta tcagcatgtg aatgtaccga agttgatcg taaagttgtt    240
agcctggtag tgcgaccttt ctcttcaggt gctttctcta tctctggagt gatttcgcca    300
gcccatgcct atctactaga gtgtctaccc cagcttgagc aggcgatggc ttttgttgct    360
tcacctgagt cttttccagg cttccgacgtc gcgaagcgct tgccataaa gccaggtatg    420
agcctccagg atgccatcac tgcctttatt aactttgtgt ccgcgatgct gaaaatgacg    480
gtgactcgtc aaaactttga cgttattgtg gctgagatcg agaggcttgc ttcaaccagc    540
gtgtccgtca ggactgaaga agcgaaggtt gctgatgagg agctaatgct attcgggtta    600
gatcatagag ggccacagca gctggatgtt tctgacgcta aagggataat gaaggctgct    660
```

```
gatattcaga caactcatga tgtccatttg gcaccaggcg ttggtaatat tgatcctgaa    720
atctataacg aggggcggtt catgttcatg cagcacaagc cacttgcggc ggatcaatcg    780
tatttcacct tggagactgc ggattatttc aagatttatc aacatacga tgaacatgat    840 ggcaggatgg ctgaccaaaa gcagtcggga ttgatactgt gtactaagga cgaggtattg    900
gctgagcaaa ctatatttaa actggacgcc cctgatgaca agactgttca tctgttggat    960
cgcgatgacg accacgttgt tgccagattt actaaggtat ttatagagga cgtggctccc   1020
gggcatcatg ctgctcaaag atcgggacaa cgctctgtgc ttgatgacct atatgcgaat   1080
acgcaagtga tttccattac ttctgctgct ttaaagtggg tggtcaagca cggcgtatct   1140
gatggaatcg tgaacaggaa gaatgtcaaa gtgtgtgttg gttttgaccc cctgtacacc   1200
ttgtctacac ataacggggt gtccttatgt gccctgctga tggacgaaaa actctctgtg   1260
ctgaacagtg cgtgtcgtat gacgttacgc tcactcatga agaccggacg cgacgttgat   1320
gcacacagag ctttttcagcg agtcctctct caaggataca catcgctaat gtgctactat   1380
catccttcac ggaagttggc atatggtgag gtgctctttc tagaacgatc caatgacgtg   1440
acagatggga tcaagcttca gttggacgca tctagacagt gtcatgaatg tcctgtgttg   1500
cagcagaaag tggttgagtt agagaaacag attattatgc agaagtcaat ccagtcagac   1560
cctaccccag tggcgctgca accattgttg tctcagttgc gtgagttgtc tagtgaagtt   1620
actaggctac agatggagtt gagtcgagct cagtccctga atgctcagtt ggaggcggat   1680
gtcaagtcag ctcaatcatg tagcttggat atgtatctga gacaccacac ttgcattaat   1740
ggtcatgcta agaagatga attgcttgac gctgtgcgtg tcgcgccgga tgtgaggaga   1800
gaaatcatgg aaaagaggag tgaagtgaga caaggttggt gcgaacgtat ttctaaggaa   1860
gcagctgcca atgtcaaac tgttattgat gacctgactt tgatgaatgg aaagcaagca   1920
caagagataa cagaattacg tgattcggct gaaaaatatg agaaacagat tgcagagctg   1980
gtgagtacca tcacccaaaa ccagataacg tatcagcaag agctacaagc cttggtagcg   2040
aaaaatgtgg aattggacgc gttgaatcag cgtcaggcta agtctttgcg tattactccc   2100
tctcttctat cagccactcc tatcgattca gttgatgatg ttgctgactt aattgatttc   2160
tctgttccaa ctgatgagtt gtaaataatc cgtgatgcag tgttgcccta atcccttaag   2220
ccttcccgac ccccattcat c                                             2241
```

<210> SEQ ID NO 8
<211> LENGTH: 3854
<212> TYPE: DNA
<213> ORGANISM: Reovirus

<400> SEQUENCE: 8

```
gctacacgtt ccacgacaat gtcatccatg atactgactc agtttggacc gttcattgag     60
agcatttcag gtatcactga tcaatcgaat gacgtgtttg aagatgcagc aaaagcattc    120
tctatgttta ctcgcagcga tgtctacaag gcgctggatg aaataccttt ctctgatgat    180
gcgatgcttc caatccctcc aactatatat acgaaaccat ctcacgattc atattattac    240
attgatgctc taaaccgtgt gcgtcgcaaa acatatcagg gccctgatga cgtgtacgta    300
cctaattgtt ctattgttga attgctggag ccacatgaga ctctgacatc ttatgggcgg    360
ttgtccgagg ccatcgagaa tcgtgccaag gatggggaca gccaagccag aatcgccaca    420
acgtatggta gaatcgctga atctcaagct cgacagatta aggctccatt ggagaagttt    480
gtgttggcac tattagtggc cgaagcaggg gggtctttat atgatccagt tttgcagaag    540
```

```
tatgatgaga ttccagatct atcgcataat tgcccttat ggtgttttag agagatctgt    600
cgtcacatat ctggtccatt accagatcgg gcaccttatc tttacttatc tgcaggggtt    660
ttctggttaa tgtcaccacg aatgacgtct gcaatccctc cgctactatc cgatcttgtt    720
aatttagcta ttttgcaaca aactgcgggt ttagatccat cattagtgaa attgggagta    780
cagatatgcc ttcatgcagc agctagctca agttatgcat ggtttatctt aaagactaag    840
tctatttttc ctcaaaacac gttgcacagt atgtatgaat ctctagaagg gggatactgt    900
cctaatcttg aatggttaga gcctagatca gactataagt tcatgtacat gggagtcatg    960
ccattgtccg ctaagtatgc taggtcggcg ccgtccaatg ataagaaagc gcgggaactt   1020
ggcgagaaat atggactgag ctcagtcgtc ggtgagcttc gtaaacggac aaagacgtat   1080
gttaaacatg actttgcttc agtgaggtac attcgtgacg ctatggcatg tactagcggt   1140
attttcttgg taagaacacc caccgaaacg gtattgcaag aatatacgca gagtccggag   1200
attaaggttc ccattcccca gaaagactgg acaggcccaa taggtgaaat cagaattcta   1260
aaagatacaa caagttccat cgcgcgttac ttatatagaa catggtactt ggcagcggcg   1320
agaatggcgg ctcaaccacg tacgtgggat ccattgtttc aagcgattat gagatctcaa   1380
tacgtgacag ctaggggtgg atctggcgca gcactccgcg aatctttgta tgcaatcaat   1440
gtgtcgttac ctgatttcaa gggcttacca gtgaaggcag caactaagat attccaggcg   1500
gcacaattag cgaacttgcc gttctcccac acatcagtgg ctatactagc tgacacttca   1560
atgggattgc gaaatcaggt gcagaggcgg ccacgatcca ttatgccatt aaatgtgccc   1620
cagcagcagg tttcggcgcc ccatacattg acagcggatt acattaacta ccacatgaat   1680
ctatcaacca cgtctggtag tgcggtcatt gagaaggtga ttcctttagg tgtatacgct   1740
tcgagccctc ctaaccagtc gatcaacatt gacatatctg cgtgtgacgc tagtattact   1800
tgggatttct ttctgtcagt gattatggcg gctatacacg aaggtgtcgc tagtagctcc   1860
attggaaaac catttatggg ggttcctgca tccattgtaa atgatgagtc tgtcgttgga   1920
gtgagagctg ctaggccgat atcgggaatg cagaacatga ttcagcatct atcgaaacta   1980
tataaacgtg gattttcata tagagtaaac gattcttttt ctccaggtaa cgatttact   2040 catatgacta ccactttccc gtcaggttca acagccacct ctactgagca tactgctaat   2100
aatagtacga tgatggaaac tttcctgaca gtatggggac ccgaacatac tgacgaccct   2160
gacgtcttac gtttaatgaa gtctttaact attcaaagga attacgtatg tcaaggtgat   2220
gatggattaa tgattatcga tgggactact gctggtaagg tgaacagtga aactattcag   2280
aagatgctag aattaatctc aaaatatggt gaggaattcg gatggaaata tgacatagcg   2340
tacgatggga ctgccgaata cttaaagcta tacttcatat ttggctgtcg aattccaaat   2400
cttagtcgcc atccaatcgt ggggaaagaa cgggcgaatt cttcagcaga ggagccatgg   2460
ccagcaattc tagatcagat tatgggtgtc ttctttaatg tgttcatga tgggttacag   2520 tggcagcggt ggatacgtta ttcatgggct ctatgctgtg ctttctcacg tcaaagaaca   2580
atgattggtg agagcgtggg ttaccttcaa tatcctatgt ggtcttttgt ctactgggga   2640
ttaccactgg ttaaagcgtt tgggtcagac ccatggatat tttcttggta catgcctact   2700
ggagatctgg gaatgtatag ttggattagc ttgatacgcc ctctgatgac aagatggatg   2760
gtggctaatg gttacgtaac tgacagatgc tcacccgtat tcgggaacgc agattatcgc   2820
aggtgtttca tgaacttaa actatatcaa ggttattata tggcacaatt gcccaggaat   2880
cctaagaagt ctggacgagc ggcccctcgg gaggtaagag aacaattcac tcaggcatta   2940
```

```
tccgactatc tactgcaaaa tccagagctg aagtcacgtg tgctacgtgg tcgtagtgag      3000
tgggagaaat atggagcggg gataattcac aatcctccgt cattattcga tgtgccccat      3060
aaatggtatc agggtgcgca agaggcagca atcgctacga gagaagagct ggcagaaatg      3120
gatgagacat taatgcgcgc tcgaaggcac agatattcga gcttttcaaa gttattagag      3180
gcgtatctgc tcgtgaaatg gcgaatgtgc gaggcccgcg aaccgtcggt ggatttgcga      3240
ttaccattat gtgcgggtat tgacccatta aactcagatc ctttctcaa gatggtaagc       3300 gttggaccaa tgctccagag tacgagaaag tactttgctc agacactatt catggcaaag      3360
acggtgtcgg gtcttgacgt taacgcgatt gatagcgcgt tattacgact gcgaacatta      3420
ggtgctgata agaaagcatt aacggcgcag ttattaatgg tggggcttca ggagtcagaa      3480
gcggacgcat tggccgggaa gataatgcta caggatgtga atactgtgca attagccaga      3540
gtggttaact tagctgtgcc agatacttgg atgtcgttag actttgactc tatgttcaaa      3600
caccacgtca agctgcttcc caaagatgga cgtcatctaa atactgatat tcctcctcga      3660
atgggatggt tacgggccat tttacgattc ttaggtgccg gaatggtaat gactgcgact      3720
ggagttgctg tcgacatcta tctggaggat atacatggcg gtggtcggtc acttggacag      3780
agattcatga cttggatgcg acaggaagga cggtcagcgt gagtctacca tgggtcgtgg      3840
tgcgtcaact catc                                                       3854

<210> SEQ ID NO 9
<211> LENGTH: 3916
<212> TYPE: DNA
<213> ORGANISM: Reovirus

<400> SEQUENCE: 9
gctaaatggc gcgatggcga acgtttgggg ggtgagactt gcagactcgt tatcttcacc        60
cactattgag acacgaacgc gtcagtatac cttacacgat cttttgctcag acctagatgc      120 taatccgggg agggaaccgt ggaaacctct gcgtaatcag cgtactaata atattgtggc       180
tgtgcaatta ttcagaccat tgcagggttt agttttagat acccagccttt atggatttcc     240 aggagcattt tgatgactggg agcgattcat gagagagaag ctgcgtgtgc taaagtatga     300
agtattgcgc atctatccaa tcagcaacta tagcaatgaa catgtcaacg tcttcgtggc      360
caatgctttg gtgggcgctt tcctgtcgaa tcaagctttc tatgacctgc taccgttgtt      420
gataattaat gacactatga ttggtgatct acttggcacg ggggcatcgc tatcacagtt      480 cttttcaatct catggagatg tgctggaagt cgcagctggt cgtaagtatc tgcagatgga      540
aaactactcc aacgatgacg atgatcctcc attatttgcg aaagacctgt cagattatgc      600
taaagcattc tacagtgaca catatgaagt gttggacagg ttcttttgga cgcatgactc       660
ttcagcgggg gtcttagtgc attatgataa gccaacgaat ggtcatcact atctgctggg      720
tactttgact cagatggtca gtgcacctcc ttatattatt aacgctactg acgcaatgtt      780
gcttgaatcc tgtctagaac agttctcagc taatgtgcgt gcgagacctg cgcaacccgt      840
tacacgctta gaccaatgct atcatttaag atggggagca caatatgtag gagaagattc      900
actgacatat cggttggggg tgttatcctt gctggctacc aatggatatc aattagctag      960
accgattcca agacagttga cgaatcgatg ttgtcgagc tttgtgagtc aaattatgtc       1020
tgacggcgtc aacgagactc cactgtggcc ccaagaaagg tatgtgcaga tcgcttatga     1080
ttcaccatcc gttgttgatg gggctacgca atatggctat gtcaggaaga atcaactcag     1140
actcggcatg agaatatcgg cgctgcaatc gctgagtgat acgccctcgc cggtacagtg     1200
```

```
gcttccacaa tacaccatcg accaggcagc gatggacgaa ggcgatctga tggttagtcg    1260
gcttacgcaa ctcccgttac gtcctgatta tggtaatatc tgggtcggcg atgcgctatc    1320
ctattatgtg gactacaatc ggagtcatcg agtcgtgctt tcatcggaac ttcctcagct    1380
tccggacaca tattttgatg gcgatgaaca gtatgggcgc agcctgttct cactagctcg    1440
taagattggt gaccgctcgt tagtgaaaga tacggctgtc ttgaagcacg cttaccaagc    1500
catcgatcca aatactggta aggagtatct gagatctcgg caatctgtcg catattttgg    1560
tgcatcagcg ggtcattctg gtgccgacca gccgttagtc atagagccct ggattcaagg    1620
gaaaatcagt ggtgtgccgc caccctcctc agtgcgacag ttcggctatg atgttgcccg    1680
tggcgcgatc gtcgatctgg cgagaccatt tccttctgga gattatcaat ttgtctattc    1740
ggatgttgac caggtggtcg atggccatga cgatctgagt atatcatctg gactggtgga    1800
gagccttttg tcttcatgca tgcacgccac agcacccggg ggctcatttg ttgttaagat    1860
aaattttccg actagacccg tatggcacta catcgaacag aagatcttgc ccaatattac    1920
gtcatacatg ttgatcaagc ctttcgtcac caacaacgtc gaattgttct tcgtcgcttt    1980
cggtgtgcat caacactcat cacttacttg gacatctgga gtgtacttct tcttggtgga    2040
ccattttat cgttatgaga ctttatctac gatctcacga caattgccgt cttttgggta     2100
tgttgatgat gggtcttccg tgactggtat cgagacaatt agtattgaga accctggctt    2160
ctcgaatatg acccaggccg ctcgcattgg tatctcagga ttgtgtgcta atgtaggtaa    2220
cgcgcgtaag tccattgcca tttacgaatc tcatggggcc agagtattaa ctatcacatc    2280
aaggagatct ccggcatcag ctagaagaaa gtctaggttg cgatatttgc cattaataga    2340
ccctaggtcg ttagaggtac aggcgcgcac tattctgcca gctgatccag tgttatttga    2400
aaacgtgagc ggagcgtcac cccatgtttg tctgacaatg atgtacaact tcgaagtgtc    2460
gtcagcggta tatgatggag acgttgtgct agatctgggg acgggaccag aggctaaaat    2520
ccttgaactg atacccgcaa cctctccagt cacatgcgtg gacatacggc ctacagcgca    2580
gcctagtgga tgttggaacg ttcgtaccac gttccttgag ttagattatt tgagcgatgg    2640
atggatcact ggggtgcgtg gggacatagt tacttgtatg ttatctttgg gggccgctgc    2700
cgctggaaaa tcaatgactt ttgacgctgc gtttcagcaa ttaatcaaag tattatccaa    2760
gagtacggct aatgttgtgc tggtgcaggt taactgccct acagacgtgg tgaggagcat    2820
taagggctac ctagagatag attcgactaa caagaggtat aggttccca aatttggtcg     2880
agacgagccg tactctgaca tggatgcgct ggagaaaata tgtcgtaccg cctggccaaa    2940
ctgctcaatt acctgggttc cattgtcata cgacttgcgg tggactagac tggcattatt    3000
agagtccacg acattgagta gcgcgtcgat tagaattgct gagctgatgt ataaatacat    3060
gcctattatg aggattgata ttcatggact acccatggaa aagcgaggta acttcatagt    3120
ggggcagaac tgctcattag taatccctgg ttttaatgcg caggatgtct ttaactgtta    3180
tttcaattcc gccctcgctt tctcgactga agatgtcaat gctgcgatga ttccccaagt    3240
gtctgcgcag tttgatgcga ctaagggtga gtggacgttg gatatggtct ctccgacgc    3300
aggaatctat accatgcagg ctctagtggg atctaatgct aatccagtct ctttgggttc    3360
ctttgtagtt gattctccag atgtagatat aactgacgct tggccagctc agttagactt    3420
tacgatcgcg ggaactgatg tcgatataac agttaatcct tattaccgtc tgatgacctt    3480
tgtaaggatc gatggacagt ggcagattgc caatccagac aaatttcaat tcttttcgtc    3540
ggcgtctggg acgttagtga tgaacgtcaa attagatatc gcagataaat atctactata    3600
```

```
ctatatacga gatgtccagt ctcgagatgt tggcttttac attcagcatc cacttcaact    3660
tttgaatacg atcacattgc caaccaacga ggacctttt  ctgagcgcac ctgacatgcg    3720
agagtgggca gttaaggaaa gcggtaacac gatatgtata ctcaatagtc aagggtttgt    3780
gctacctcaa gattgggatg tgttaacaga taccataagt tggtcccat  cgatacccac    3840 atacattgtg ccaccgggtg attatacctt gactcctctg taactcactg tccctcgtga    3900
gcgcgcctaa ttcatc                                                    3916

<210> SEQ ID NO 10
<211> LENGTH: 3901
<212> TYPE: DNA
<213> ORGANISM: Reovirus

<400> SEQUENCE: 10
gctaatcgtc aggatgaagc ggattccaag gaagacaaag ggcaaatcca gcggaaaggg      60
caatgactca acagagagag cggacgatgg ctcgagccaa ttaagagaca agcaaaacaa     120
taaggctggc cccgccacta cggagcctgg cacatccaac cgagagcaat acaaagctcg     180
accaggtatt gcatctgtgc agagggccac tgaaagtgca gaaatgccca tgaagaataa     240
tgacgaaggg acgccagata agaaaggaaa tactaagggc gacctagtta atgagcatag     300
tgaggctaaa gacgaggcgg atgaagcgac gaagaagcag gcaaaggata cagacaaaag     360
taaagcgcaa gtcacatatt cagacactgg tatcaataat gctaatgaac tgtcaagatc     420
tgggaatgtg gataatgagg gtggaagtaa tcagaagccg atgtctacca gaatagctga     480
ggcaacgtct gctatagtgt cgaaacatcc tgcgcgtgtt gggctgccac ctaccgctag     540
cagtggtcat gggtatcagt gccatgtctg ttctgcagtc ctgtttagtc ctttagacct     600
agatgcccac gtcgcctcac atggtttgca tggtaacatg acattaacat cgagtgatat     660
ccagcgacat ataactgagt tcatcagctc atggcaaaat catcctattg ttcaagtttc     720
ggctgatgtc gaaaataaga aaactgctca attgcttcac gctgacactc ctcgactcgt     780
cacttgggat gctggtttgt gtacttcatt caaaatcgtc ccgattgtgc cagctcaggt     840
gccgcaggat gtactggcct atcgtttttt cacctcttca tacgctatcc aatcaccgtt     900
tccagaggcg gcagtgtcta ggattgtggt gcatacgaga tgggcatcta atgttgactt     960
tgaccgagac tcgtctgtca tcatggcgcc acctacagaa aacaatatcc atttgtttaa    1020
acagttacta aatactgaaa ccctgtctgt aagggggggct aatccgctaa tgttcagggc    1080
gaatgtgttg catatgttgc tagagttcgt attagataac ttgtatctga acagacatac    1140
gggattctct caagaccaca cgccatttac tgagggtgct aatttgcgtt cacttcctgg    1200
ccccgatgct gagaaatggt actcgattat gtatccaacg cgcatgggaa cgccgaatgt    1260
atccaaaata tgtaatttcg tcgcctcttg tgtgcgaaat cgggttggac ggtttgatcg    1320
agcacagatg atgaacggag ctatgtcaga gtgggtggat gtcttcgaga cttcagacgc    1380
gctaaccgtc tccattcgag gtcgatggat ggctagacta gctcgcatga acataaatcc    1440
aacagagatc gaatgggcat tgactgaatg tgcacaagga tatgtgactg tcacaagtcc    1500
ttacgctcct agcgtaaata gattgatgcc ctatcgtatc tccaacgctg agcggcaaat    1560
atcacagata tcaggatca  tgaacattgg caataacgcg acggtgatac aacctgttct    1620
gcaagatatt tcggtactcc ttcaacgcat atcaccactc caaatagatc caactattat    1680
ttccaacact atgtcaacag tctcggagtc tactactcag accctcagcc ccgcgtcctc    1740
aattttgggt aaactacgac caagcaactc agattttct  agttttagag tcgcgttggc    1800
```

-continued

```
tggatggctt tataatgggg ttgtgacgac ggtgattgat gatagttcat atccaaaaga    1860
cggcggcagc gtgacctcac ttgaaaatct gtgggatttc ttcatccttg cgcttgctct    1920
accactgaca actgacccct gtgcacctgt gaaagcattc atgaccctag ccaacatgat    1980
ggttggtttc gagacaatcc ctatggataa tcagatctat actcaatcga cgcgcgag     2040
tgctttctca acgcctcaca cgtggccacg atgctttatg aacatccagt taatttctcc    2100
aatcgacgct cccatcttgc gacagtgggc tgaaattatt catagatact ggcctaaccc    2160
ttcacagatt cgttatggtg caccgaacgt tttcggctcg gcaaatttgt tcactccacc    2220
tgaggtgctg ttattgccaa tcgatcatca accagctaat gtaacaacgc caacgctgga    2280
cttcaccaat gagttaacta attggcgcgc tcgtgtctgt gagcttatga agaatctcgt    2340
tgataaccaa agatatcaac ctggatggac acaaagtcta gtctcgtcaa tgcgcggaac    2400
gctagacaaa ttgaagttga ttaaatcgat gacaccaatg tatctgcaac agctggctcc    2460
ggtagagtta gcagtgatag ctcccatgtt gccttttcca cctttccagg tgccatacgt    2520
ccgtctcgat cgtgacagag ttccaacaat ggttggagta acacgacatt cacgagatac    2580
tattactcag ccggcgctat cgctgtcgac aaccaatact actgttggcg tgccactagc    2640
tctagacgcg agggctatca ccgttgcgct gttgtcaggg aaatatccgc cggatttggt    2700
gacaaatgta tggtacgctg atgccattta cccaatgtat gcagacacgg aggtgttctc    2760
taatcttcag agagacatga ttacctgcga ggccgtgcag acattagtga ctctggtggc    2820
gcaaatatca gagacccagt atcctgtaga taggtatctt gattggatcc catcactgag    2880
agcatcggcg gcgacggcgg cgacatttgc tgagtgggtt aatacttcaa tgaagacggc    2940
gtttgatttg tctgatatgc tgttagagcc tctcctaagc ggtgatccga ggatgactca    3000
actagcgatt cagtatcagc agtacaatgg cagaacgttt aatatcatac ctgaaatgcc    3060
aggttcagta attgctgact gcgttcaatt aacagcagaa gtctttaatc acgaatataa    3120
cctgtttggg attgcgcggg gtgatatcat cattggccgt gttcagtcga cacatttgtg    3180
gtcaccgctg gctcctccac ctgacctggt gtttgatcgt gataccctg gtgttcacat      3240
cttcggacga gattgccgta tatcgttggg aatgaatggc gccgcgccaa tgattagaga    3300
tgagactgga ctgatggtgc cttttgaagg aaattggatt ttcccactgg cgctttggca    3360
aatgaataca cgatattta atcaacagtt cgacgcgtgg attaagacag agagttgcg     3420
aatccgcatt gagatgggcg cgtatccata tatgttgcat tactatgatc cacgtcagta    3480
cgctaatgca tggaatttaa catccgcctg gcttgaagaa attacgccga cgagcatccc    3540
atccgtgcct ttcatggtgc ccatttcaag tgatcatgac attttcctctg ccccagctgt    3600
ccaatatatc atttcaactg aatataatga tcggtctctg ttctgcacta actcatcatc    3660
tccccaaacc atcgctggac cagacaaaca cattccagtt gagagatata acattctgac    3720
caaccccgac gctccaccca cgcagataca actgcctgaa gtcgttgact tgtacaacgt    3780
cgtcacacgc tatgcgtatg agactccgcc tattaccgct gttgttatgg gtgttccttg    3840
atcctcatcc tcccaacagg tgctagagca ttgcgctcaa tgctagttgg gccgattcat    3900
c                                                                     3901
```

<210> SEQ ID NO 11
<211> LENGTH: 455
<212> TYPE: PRT
<213> ORGANISM: Reovirus

<400> SEQUENCE: 11

```
Met Asp Pro Arg Leu Arg Glu Glu Val Val Arg Leu Ile Ile Ala Leu
 1               5                  10                  15

Thr Ser Asp Asn Gly Ala Ser Leu Ser Lys Gly Leu Glu Ser Arg Val
             20                  25                  30

Ser Ala Leu Glu Lys Thr Ser Gln Ile His Ser Asp Thr Ile Leu Arg
         35                  40                  45

Ile Thr Gln Gly Leu Asp Asp Ala Asn Lys Arg Ile Ile Ala Leu Glu
     50                  55                  60

Gln Ser Arg Asp Asp Leu Val Ala Ser Val Ser Asp Ala Gln Leu Ala
 65                  70                  75                  80

Ile Ser Arg Leu Glu Ser Ser Ile Gly Ala Leu Gln Thr Val Val Asn
                 85                  90                  95

Gly Leu Asp Ser Ser Val Thr Gln Leu Gly Ala Arg Val Gly Gln Leu
                100                 105                 110

Glu Thr Gly Leu Ala Glu Leu Arg Val Asp His Asp Asn Leu Val Ala
            115                 120                 125

Arg Val Asp Thr Ala Glu Arg Asn Ile Gly Ser Leu Thr Thr Glu Leu
        130                 135                 140

Ser Thr Leu Thr Leu Arg Val Thr Ser Ile Gln Ala Asp Phe Glu Ser
145                 150                 155                 160

Arg Ile Ser Thr Leu Glu Arg Thr Ala Val Thr Ser Ala Gly Ala Pro
                165                 170                 175

Leu Ser Ile Arg Asn Asn Arg Met Thr Met Gly Leu Asn Asp Gly Leu
                180                 185                 190

Thr Leu Ser Gly Asn Asn Leu Ala Ile Arg Leu Pro Gly Asn Thr Gly
        195                 200                 205

Leu Asn Ile Gln Asn Gly Gly Leu Gln Phe Arg Phe Asn Thr Asp Gln
    210                 215                 220

Phe Gln Ile Val Asn Asn Asn Leu Thr Leu Lys Thr Thr Val Phe Asp
225                 230                 235                 240

Ser Ile Asn Ser Arg Ile Gly Ala Thr Glu Gln Ser Tyr Val Ala Ser
                245                 250                 255

Ala Val Thr Pro Leu Arg Leu Asn Ser Ser Thr Lys Val Leu Asp Met
                260                 265                 270

Leu Ile Asp Ser Ser Thr Leu Glu Ile Asn Ser Ser Gly Gln Leu Thr
        275                 280                 285

Val Arg Ser Thr Ser Pro Asn Leu Arg Tyr Pro Ile Ala Asp Val Ser
    290                 295                 300

Gly Gly Ile Gly Met Ser Pro Asn Tyr Arg Phe Arg Gln Ser Met Trp
305                 310                 315                 320

Ile Gly Ile Val Ser Tyr Ser Gly Ser Gly Leu Asn Trp Arg Val Gln
                325                 330                 335

Val Asn Ser Asp Ile Phe Ile Val Asp Asp Tyr Ile His Ile Cys Leu
            340                 345                 350

Pro Ala Phe Asp Gly Phe Ser Ile Ala Asp Gly Gly Asp Leu Ser Leu
        355                 360                 365

Asn Phe Val Thr Gly Leu Leu Pro Pro Leu Leu Thr Gly Asp Thr Glu
    370                 375                 380

Pro Ala Phe His Asn Asp Val Val Thr Tyr Gly Ala Gln Thr Val Ala
385                 390                 395                 400

Ile Gly Leu Ser Ser Gly Gly Ala Pro Gln Tyr Met Ser Lys Asn Leu
                405                 410                 415

Trp Val Glu Gln Trp Gln Asp Gly Val Leu Arg Leu Arg Val Glu Gly
                420                 425                 430
```

```
Gly Gly Ser Ile Thr His Ser Asn Ser Lys Trp Pro Ala Met Thr Val
            435                 440                 445

Ser Tyr Pro Arg Ser Phe Thr
        450             455

<210> SEQ ID NO 12
<211> LENGTH: 418
<212> TYPE: PRT
<213> ORGANISM: Reovirus

<400> SEQUENCE: 12

Met Ala Arg Ala Ala Phe Leu Phe Lys Thr Val Gly Phe Gly Gly Leu
  1               5                  10                  15

Gln Asn Val Pro Ile Asn Asp Glu Leu Ser Ser His Leu Leu Arg Ala
             20                  25                  30

Gly Asn Ser Pro Trp Gln Leu Thr Gln Phe Leu Asp Trp Ile Ser Leu
         35                  40                  45

Gly Arg Gly Leu Ala Thr Ser Ala Leu Val Pro Thr Ala Gly Ser Arg
     50                  55                  60

Tyr Tyr Gln Met Ser Cys Leu Leu Ser Gly Thr Leu Gln Ile Pro Phe
 65                  70                  75                  80

Arg Pro Asn His Arg Trp Gly Asp Ile Arg Phe Leu Arg Leu Val Trp
                 85                  90                  95

Ser Ala Pro Thr Leu Asp Gly Leu Val Val Ala Pro Pro Gln Val Leu
            100                 105                 110

Ala Gln Pro Ala Leu Gln Ala Gln Ala Asp Arg Val Tyr Asp Cys Asp
        115                 120                 125

Asp Tyr Pro Phe Leu Ala Arg Asp Pro Arg Phe Lys His Arg Val Tyr
    130                 135                 140

Gln Gln Leu Ser Ala Val Thr Leu Leu Asn Leu Thr Gly Phe Gly Pro
145                 150                 155                 160

Ile Ser Tyr Val Arg Val Asp Glu Asp Met Trp Ser Gly Asp Val Asn
                165                 170                 175

Gln Leu Leu Met Asn Tyr Phe Gly His Thr Phe Ala Glu Ile Ala Tyr
            180                 185                 190

Thr Leu Cys Gln Ala Ser Ala Asn Arg Pro Trp Glu Tyr Asp Gly Thr
        195                 200                 205

Tyr Ala Arg Met Thr Gln Ile Val Leu Ser Leu Phe Trp Leu Ser Tyr
    210                 215                 220

Val Gly Val Ile His Gln Asn Thr Tyr Arg Thr Phe Tyr Phe Gln
225                 230                 235                 240

Cys Asn Arg Arg Gly Asp Ala Ala Glu Val Trp Ile Leu Ser Cys Ser
                245                 250                 255

Leu Asn His Ser Ala Gln Ile Arg Pro Gly Asn Arg Ser Leu Phe Val
            260                 265                 270

Met Pro Thr Ser Pro Asp Trp Asn Met Asp Val Asn Leu Ile Leu Ser
        275                 280                 285

Ser Thr Leu Thr Gly Cys Leu Cys Ser Gly Ser Gln Leu Pro Leu Ile
    290                 295                 300

Asp Asn Asn Ser Val Pro Ala Val Ser Arg Asn Ile His Gly Trp Thr
305                 310                 315                 320

Gly Arg Ala Gly Asn Gln Leu His Gly Phe Gln Val Arg Arg Met Val
                325                 330                 335

Thr Glu Phe Cys Asp Arg Leu Arg Arg Asp Gly Val Met Thr Gln Ala
            340                 345                 350
```

```
Gln Gln Asn Gln Val Glu Ala Leu Ala Asp Gln Thr Gln Gln Phe Lys
            355                 360                 365

Arg Asp Lys Leu Glu Thr Trp Ala Arg Glu Asp Gln Tyr Asn Gln
        370                 375                 380

Ala His Pro Asn Ser Thr Met Phe Arg Thr Lys Pro Phe Thr Asn Ala
385                 390                 395                 400

Gln Trp Gly Arg Gly Asn Thr Gly Ala Thr Ser Ala Ala Ile Ala Ala
                405                 410                 415

Leu Ile

<210> SEQ ID NO 13
<211> LENGTH: 254
<212> TYPE: PRT
<213> ORGANISM: Reovirus

<400> SEQUENCE: 13

Met Ala Ser Ser Leu Arg Ala Ala Ile Ser Lys Ile Lys Arg Asp Asp
 1               5                  10                  15

Val Gly Gln Gln Val Cys Pro Asn Tyr Val Met Leu Arg Ser Ser Val
            20                  25                  30

Thr Thr Lys Val Val Arg Asn Val Val Glu Tyr Gln Ile Arg Thr Gly
        35                  40                  45

Gly Phe Phe Ser Cys Leu Ala Met Leu Arg Pro Leu Gln Tyr Ala Lys
    50                  55                  60

Arg Glu Arg Leu Leu Gly Gln Arg Asn Leu Glu Arg Ile Ser Thr Arg
65                  70                  75                  80

Asp Ile Leu Gln Thr Arg Asp Leu His Ser Leu Cys Met Pro Thr Pro
                85                  90                  95

Asp Ala Pro Met Ser Asn His Gln Ala Ser Thr Met Arg Glu Leu Ile
            100                 105                 110

Cys Ser Tyr Phe Lys Val Asp His Ala Asp Gly Leu Lys Tyr Ile Pro
        115                 120                 125

Met Asp Glu Arg Tyr Ser Pro Ser Ser Leu Ala Arg Leu Phe Thr Met
    130                 135                 140

Gly Met Ala Gly Leu His Ile Thr Thr Glu Pro Ser Tyr Lys Arg Val
145                 150                 155                 160

Pro Ile Met His Leu Ala Ala Asp Leu Asp Cys Met Thr Leu Ala Leu
                165                 170                 175

Pro Tyr Met Ile Thr Leu Asp Gly Asp Thr Val Val Pro Val Ala Pro
            180                 185                 190

Thr Leu Ser Ala Glu Gln Leu Leu Asp Asp Gly Leu Lys Gly Leu Ala
        195                 200                 205

Cys Met Asp Met Asp Val Arg Trp Thr Arg Ile Ala Gly Arg Leu Val
    210                 215                 220

Ile Arg Val Trp Thr Leu His Ala Ala Ser Thr Ser Cys Ile Ala Arg
225                 230                 235                 240

Arg Gln Gln Lys Pro Ser Val Cys Leu Arg His Ala Leu Cys
                245                 250

<210> SEQ ID NO 14
<211> LENGTH: 366
<212> TYPE: PRT
<213> ORGANISM: Reovirus

<400> SEQUENCE: 14

Met Ala Ser Ser Leu Arg Ala Ala Ile Ser Lys Ile Lys Arg Asp Asp
```

```
            1               5                  10                 15
        Val Gly Gln Gln Val Cys Pro Asn Tyr Val Met Leu Arg Ser Ser Val
                        20                 25                 30

Thr Thr Lys Val Val Arg Asn Val Val Glu Tyr Gln Ile Arg Thr Gly
                        35                 40                 45

Gly Phe Phe Ser Cys Leu Ala Met Leu Arg Pro Leu Gln Tyr Ala Lys
                        50                 55                 60

Arg Glu Arg Leu Leu Gly Gln Arg Asn Leu Arg Ile Ser Thr Arg
         65                 70                 75                 80

Asp Ile Leu Gln Thr Arg Asp Leu His Ser Leu Cys Met Pro Thr Pro
                        85                 90                 95

Asp Ala Pro Met Ser Asn His Gln Ala Ser Thr Met Arg Glu Leu Ile
                       100                105                110

Cys Ser Tyr Phe Lys Val Asp His Ala Asp Gly Leu Lys Tyr Ile Pro
                       115                120                125

Met Asp Glu Arg Tyr Ser Pro Ser Ser Leu Ala Arg Leu Phe Thr Met
                       130                135                140

Gly Met Ala Gly Leu His Ile Thr Thr Glu Pro Ser Tyr Lys Arg Val
        145                150                155                160

Pro Ile Met His Leu Ala Ala Asp Leu Asp Cys Met Thr Leu Ala Leu
                       165                170                175

Pro Tyr Met Ile Thr Leu Asp Gly Asp Thr Val Val Pro Val Ala Pro
                       180                185                190

Thr Leu Ser Ala Glu Gln Leu Leu Asp Asp Gly Leu Lys Gly Leu Ala
                       195                200                205

Cys Met Asp Ile Ser Tyr Gly Cys Glu Val Asp Ala Asn Ser Arg Pro
                       210                215                220

Ala Gly Asp Gln Ser Met Asp Ser Ser Arg Cys Ile Asn Glu Leu Tyr
        225                230                235                240

Cys Glu Glu Thr Ala Glu Ala Ile Cys Val Leu Lys Thr Cys Leu Val
                       245                250                255

Leu Asn Cys Met Gln Phe Lys Leu Glu Met Asp Asp Leu Ala His Asn
                       260                265                270

Ala Ala Glu Leu Asp Lys Ile Gln Met Met Ile Pro Phe Ser Glu Arg
                       275                280                285

Val Phe Arg Met Ala Ser Ser Phe Ala Thr Ile Asp Ala Gln Cys Phe
                       290                295                300

Arg Phe Cys Val Met Met Lys Asp Lys Asn Leu Lys Ile Asp Met Arg
        305                310                315                320

Glu Thr Thr Arg Leu Trp Thr Arg Ser Ala Ser Asp Asp Ser Val Ala
                       325                330                335

Thr Ser Ser Leu Ser Ile Ser Leu Asp Arg Gly Arg Trp Val Ala Ala
                       340                345                350

Asp Ala Ser Asp Ala Arg Leu Leu Val Phe Pro Ile Arg Val
                       355                360                365

<210> SEQ ID NO 15
<211> LENGTH: 365
<212> TYPE: PRT
<213> ORGANISM: Reovirus

<400> SEQUENCE: 15

Met Glu Val Cys Leu Pro Asn Gly His Gln Val Val Asp Leu Ile Asn
         1               5                  10                 15

Asn Ala Phe Glu Gly Arg Val Ser Ile Tyr Ser Ala Gln Glu Gly Trp
```

```
                    20                  25                  30
Asp Lys Thr Ile Ser Ala Gln Pro Asp Met Met Val Cys Gly Gly Ala
            35                  40                  45

Val Val Cys Met His Cys Leu Gly Val Val Gly Ser Leu Gln Arg Lys
        50                  55                  60

Leu Lys His Leu Pro His His Arg Cys Asn Gln Gln Ile Arg His Gln
65                  70                  75                  80

Asp Tyr Val Asp Val Gln Phe Ala Asp Arg Val Thr Ala His Trp Lys
                85                  90                  95

Arg Gly Met Leu Ser Phe Val Ala Gln Met His Glu Met Met Asn Asp
            100                 105                 110

Val Ser Pro Asp Asp Leu Asp Arg Val Arg Thr Glu Gly Gly Ser Leu
        115                 120                 125

Val Glu Leu Asn Arg Leu Gln Val Asp Pro Asn Ser Met Phe Arg Ser
    130                 135                 140

Ile His Ser Ser Trp Thr Asp Pro Leu Gln Val Val Asp Asp Leu Asp
145                 150                 155                 160

Thr Lys Leu Asp Gln Tyr Trp Thr Ala Leu Asn Leu Met Ile Asp Ser
                165                 170                 175

Ser Asp Leu Ile Pro Asn Phe Met Met Arg Asp Pro Ser His Ala Phe
            180                 185                 190

Asn Gly Val Lys Leu Lys Gly Asp Ala Arg Gln Thr Gln Phe Ser Arg
        195                 200                 205

Thr Phe Asp Ser Arg Ser Ser Leu Glu Trp Gly Val Met Val Tyr Asp
    210                 215                 220

Tyr Ser Glu Leu Asp His Asp Pro Ser Lys Gly Arg Ala Tyr Arg Lys
225                 230                 235                 240

Glu Leu Val Thr Pro Ala Arg Asp Phe Gly His Phe Gly Leu Ser His
                245                 250                 255

Tyr Ser Arg Ala Thr Thr Pro Ile Leu Gly Lys Met Pro Ala Val Phe
            260                 265                 270

Ser Gly Met Leu Thr Gly Asn Cys Lys Met Tyr Pro Phe Ile Lys Gly
        275                 280                 285

Thr Ala Lys Leu Lys Thr Val Arg Lys Leu Val Glu Ala Val Asn His
    290                 295                 300

Ala Trp Gly Val Glu Lys Ile Arg Tyr Ala Leu Gly Pro Gly Gly Met
305                 310                 315                 320

Thr Gly Trp Tyr Asn Arg Thr Met Gln Gln Ala Pro Ile Val Leu Thr
                325                 330                 335

Pro Ala Ala Leu Thr Met Phe Pro Asp Thr Ile Lys Phe Gly Asp Leu
            340                 345                 350

Asn Tyr Pro Val Met Ile Gly Asp Pro Met Ile Leu Gly
        355                 360                 365

<210> SEQ ID NO 16
<211> LENGTH: 736
<212> TYPE: PRT
<213> ORGANISM: Reovirus

<400> SEQUENCE: 16

Met Ala Tyr Ile Ala Val Pro Ala Val Val Asp Ser Arg Ser Ser Glu
1               5                   10                  15

Ala Ile Gly Leu Leu Glu Ser Phe Gly Val Asp Ala Gly Ala Asp Ala
            20                  25                  30

Asn Asp Val Ser Tyr Gln Asp His Asp Tyr Val Leu Asp Gln Leu Gln
```

-continued

```
                35                  40                  45
Tyr Met Leu Asp Gly Tyr Glu Ala Gly Asp Val Ile Asp Ala Leu Val
 50                  55                  60

His Lys Asn Trp Leu His His Ser Val Tyr Cys Leu Leu Pro Pro Lys
 65                  70                  75                  80

Ser Gln Leu Leu Glu Tyr Trp Lys Ser Asn Pro Ser Ala Ile Pro Asp
                     85                  90                  95

Asn Val Asp Arg Arg Leu Arg Lys Arg Leu Met Leu Lys Lys Asp Leu
                100                 105                 110

Arg Lys Asp Asp Glu Tyr Asn Gln Leu Ala Arg Ala Phe Lys Ile Ser
                115                 120                 125

Asp Val Tyr Ala Pro Leu Ile Ser Ser Thr Thr Ser Pro Met Thr Met
                130                 135                 140

Ile Gln Asn Leu Asn Arg Gly Glu Ile Val Tyr Thr Thr Thr Asp Arg
145                 150                 155                 160

Val Ile Gly Ala Arg Ile Leu Leu Tyr Ala Pro Arg Lys Tyr Tyr Ala
                165                 170                 175

Ser Thr Leu Ser Phe Thr Met Thr Lys Cys Ile Ile Pro Phe Gly Lys
                180                 185                 190

Glu Val Gly Arg Val Pro His Ser Arg Phe Asn Val Gly Thr Phe Pro
                195                 200                 205

Ser Ile Ala Thr Pro Lys Cys Phe Val Met Ser Gly Val Asp Ile Glu
 210                215                 220

Ser Ile Pro Asn Glu Phe Ile Lys Leu Phe Tyr Gln Arg Val Lys Ser
225                 230                 235                 240

Val His Ala Asn Ile Leu Asn Asp Ile Ser Pro Gln Ile Val Ser Asp
                245                 250                 255

Met Ile Asn Arg Lys Arg Leu Arg Val His Thr Pro Ser Asp Arg Arg
                260                 265                 270

Ala Ala Gln Leu Met His Leu Pro Tyr His Val Lys Arg Gly Ala Ser
                275                 280                 285

His Val Asp Val Tyr Lys Val Asp Val Asp Met Leu Phe Glu Val
                290                 295                 300

Val Asp Val Ala Asp Gly Leu Arg Asn Val Ser Arg Lys Leu Thr Met
305                 310                 315                 320

His Thr Val Pro Val Cys Ile Leu Glu Met Leu Gly Ile Glu Ile Ala
                325                 330                 335

Asp Tyr Cys Ile Arg Gln Glu Asp Gly Met Leu Thr Asp Trp Phe Leu
                340                 345                 350

Leu Leu Thr Met Leu Ser Asp Gly Leu Thr Asp Arg Arg Thr His Cys
                355                 360                 365

Gln Tyr Leu Ile Asn Pro Ser Ser Val Pro Pro Asp Val Ile Leu Asn
                370                 375                 380

Ile Ser Ile Thr Gly Phe Ile Asn Arg His Thr Ile Asp Val Met Pro
385                 390                 395                 400

Asp Ile Tyr Asp Phe Val Lys Pro Ile Gly Ala Val Leu Pro Lys Gly
                405                 410                 415

Ser Phe Lys Ser Thr Ile Met Arg Val Leu Asp Ser Ile Ser Ile Leu
                420                 425                 430

Gly Ile Gln Ile Met Pro Arg Ala His Val Val Asp Ser Asp Glu Val
                435                 440                 445

Gly Glu Gln Met Glu Pro Thr Phe Glu Gln Ala Val Met Glu Ile Tyr
                450                 455                 460
```

```
Lys Gly Ile Ala Gly Val Asp Ser Leu Asp Asp Leu Ile Lys Trp Val
465                 470                 475                 480

Leu Asn Ser Asp Leu Ile Pro His Asp Asp Arg Leu Gly Gln Leu Phe
            485                 490                 495

Gln Ala Phe Leu Pro Leu Ala Lys Asp Leu Leu Ala Pro Met Ala Arg
        500                 505                 510

Lys Phe Tyr Asp Asn Ser Met Ser Glu Gly Arg Leu Leu Thr Phe Ser
    515                 520                 525

His Ala Asp Ser Glu Leu Leu Asn Ala Asn Tyr Phe Gly His Leu Leu
530                 535                 540

Arg Leu Lys Ile Pro Tyr Ile Thr Glu Val Asn Leu Met Ile Arg Lys
545                 550                 555                 560

Asn Arg Glu Gly Gly Glu Leu Phe Gln Leu Val Leu Ser Tyr Leu Tyr
            565                 570                 575

Lys Met Tyr Ala Thr Ser Ala Gln Pro Lys Trp Phe Gly Ser Leu Leu
        580                 585                 590

Arg Leu Leu Ile Cys Pro Trp Leu His Met Glu Lys Leu Ile Gly Glu
    595                 600                 605

Ala Asp Pro Ala Ser Thr Ser Ala Glu Ile Gly Trp His Ile Pro Arg
610                 615                 620

Glu Gln Leu Met Gln Asp Gly Trp Cys Gly Cys Glu Asp Gly Phe Ile
625                 630                 635                 640

Pro Tyr Val Ser Ile Arg Ala Pro Arg Leu Val Ile Glu Glu Leu Met
            645                 650                 655

Glu Lys Asn Trp Gly Gln Tyr His Ala Gln Val Ile Val Thr Asp Gln
        660                 665                 670

Leu Val Val Gly Glu Pro Arg Arg Val Ser Ala Lys Ala Val Ile Lys
    675                 680                 685

Gly Asn His Leu Pro Val Lys Leu Val Ser Arg Phe Ala Cys Phe Thr
690                 695                 700

Leu Thr Ala Lys Tyr Glu Met Arg Leu Ser Cys Gly His Ser Thr Gly
705                 710                 715                 720

Arg Gly Ala Ala Tyr Ser Ala Arg Leu Ala Phe Arg Ser Asp Leu Ala
            725                 730                 735

<210> SEQ ID NO 17
<211> LENGTH: 708
<212> TYPE: PRT
<213> ORGANISM: Reovirus

<400> SEQUENCE: 17

Met Gly Asn Ala Ser Ser Ile Val Gln Thr Ile Asn Val Thr Gly Asp
 1               5                  10                  15

Gly Asn Val Phe Lys Pro Ser Ala Glu Thr Ser Ser Thr Ala Val Pro
            20                  25                  30

Ser Leu Ser Leu Ser Pro Gly Met Leu Asn Pro Gly Gly Val Pro Trp
        35                  40                  45

Ile Ala Val Gly Asp Glu Thr Ser Val Thr Ser Pro Gly Ala Leu Arg
    50                  55                  60

Arg Met Thr Ser Lys Asp Ile Pro Asp Thr Ala Ile Ile Asn Thr Asp
65                  70                  75                  80

Asn Ser Ser Gly Ala Val Pro Ser Glu Ser Ala Leu Val Pro Tyr Ile
                85                  90                  95

Asp Glu Pro Leu Val Val Val Thr Glu His Ala Ile Thr Asn Phe Thr
            100                 105                 110
```

-continued

```
Lys Ala Glu Met Ala Leu Glu Phe Asn Arg Glu Phe Leu Asp Lys Met
            115                 120                 125

Arg Val Leu Ser Val Ser Pro Lys Tyr Ser Asp Leu Leu Thr Tyr Val
        130                 135                 140

Asp Cys Tyr Val Gly Val Ser Ala Arg Gln Ala Leu Asn Asn Phe Gln
145                 150                 155                 160

Lys Gln Val Pro Val Ile Thr Pro Thr Arg Gln Thr Met Tyr Val Asp
                165                 170                 175

Ser Ile Gln Ala Ala Leu Lys Ala Leu Glu Lys Trp Glu Ile Asp Leu
            180                 185                 190

Arg Val Ala Gln Thr Leu Leu Pro Thr Asn Val Pro Ile Gly Glu Val
        195                 200                 205

Ser Cys Pro Met Gln Ser Val Val Lys Leu Leu Asp Asp Gln Leu Pro
    210                 215                 220

Asp Asp Ser Leu Ile Arg Arg Tyr Pro Lys Glu Ala Val Ala Leu
225                 230                 235                 240

Ala Lys Arg Asn Gly Gly Ile Gln Trp Met Asp Val Ser Glu Gly Thr
                245                 250                 255

Val Met Asn Glu Ala Val Asn Ala Val Ala Ser Ala Leu Ala Pro
            260                 265                 270

Ser Ala Ser Ala Pro Pro Leu Glu Glu Lys Ser Lys Leu Thr Glu Gln
    275                 280                 285

Ala Met Asp Leu Val Thr Ala Ala Glu Pro Glu Ile Ile Ala Ser Leu
    290                 295                 300

Ala Pro Val Pro Ala Pro Val Phe Ala Ile Pro Pro Lys Pro Ala Asp
305                 310                 315                 320

Tyr Asn Val Arg Thr Leu Arg Ile Asp Glu Ala Thr Trp Leu Arg Met
                325                 330                 335

Ile Pro Lys Ser Met Asn Thr Pro Phe Gln Ile Gln Val Thr Asp Asn
            340                 345                 350

Thr Gly Thr Asn Trp His Leu Asn Leu Arg Gly Gly Thr Arg Val Val
        355                 360                 365

Asn Leu Asp Gln Ile Ala Pro Met Arg Phe Val Leu Asp Leu Gly Gly
    370                 375                 380

Lys Ser Tyr Lys Glu Thr Ser Trp Asp Pro Asn Gly Lys Lys Val Gly
385                 390                 395                 400

Phe Ile Val Phe Gln Ser Lys Ile Pro Phe Glu Leu Trp Thr Ala Ala
                405                 410                 415

Ser Gln Ile Gly Gln Ala Thr Val Val Asn Tyr Val Gln Leu Tyr Ala
            420                 425                 430

Glu Asp Ser Ser Phe Thr Ala Gln Ser Ile Ile Ala Thr Thr Ser Leu
        435                 440                 445

Ala Tyr Asn Tyr Glu Pro Glu Gln Leu Asn Lys Thr Asp Pro Glu Met
    450                 455                 460

Asn Tyr Tyr Leu Leu Ala Thr Phe Ile Asp Ser Ala Ala Ile Thr Pro
465                 470                 475                 480

Thr Asn Met Thr Gln Pro Asp Val Trp Asp Ala Leu Leu Thr Met Ser
                485                 490                 495

Pro Leu Ser Ala Gly Glu Val Thr Val Lys Gly Ala Val Val Ser Glu
            500                 505                 510

Val Val Pro Ala Asp Leu Ile Gly Ser Tyr Thr Pro Glu Ser Leu Asn
        515                 520                 525

Ala Ser Leu Pro Asn Asp Ala Ala Arg Cys Met Ile Asp Arg Ala Ser
    530                 535                 540
```

```
Lys Ile Ala Glu Ala Ile Lys Ile Asp Asp Ala Gly Pro Asp Glu
545                 550                 555                 560

Tyr Ser Pro Asn Ser Val Pro Ile Gln Gly Gln Leu Ala Ile Ser Gln
                565                 570                 575

Leu Glu Thr Gly Tyr Gly Val Arg Ile Phe Asn Pro Lys Gly Ile Leu
            580                 585                 590

Ser Lys Ile Ala Ser Arg Ala Met Gln Ala Phe Ile Gly Asp Pro Ser
        595                 600                 605

Thr Ile Ile Thr Gln Ala Ala Pro Val Leu Ser Asp Lys Asn Asn Trp
    610                 615                 620

Ile Ala Leu Ala Gln Gly Val Lys Thr Ser Leu Arg Thr Lys Ser Leu
625                 630                 635                 640

Ser Ala Gly Val Lys Thr Ala Val Ser Lys Leu Ser Ser Glu Ser
                645                 650                 655

Ile Gln Asn Trp Thr Gln Gly Phe Leu Asp Lys Val Ser Ala His Phe
                660                 665                 670

Pro Ala Pro Lys Pro Asp Cys Pro Thr Ser Gly Asp Ser Gly Glu Ser
            675                 680                 685

Ser Asn Arg Arg Val Lys Arg Asp Ser Tyr Ala Gly Val Val Lys Arg
690                 695                 700

Gly Tyr Thr Arg
705

<210> SEQ ID NO 18
<211> LENGTH: 721
<212> TYPE: PRT
<213> ORGANISM: Reovirus

<400> SEQUENCE: 18

Met Ala Ser Phe Lys Gly Phe Ser Ala Asn Thr Val Pro Val Ser Lys
1               5                   10                  15

Ala Lys Arg Asp Ile Ser Ser Leu Ala Ala Thr Pro Gly Leu Arg Ser
                20                  25                  30

Gln Ser Phe Thr Pro Ser Val Asp Met Ser Gln Ser Arg Glu Phe Leu
            35                  40                  45

Thr Lys Ala Ile Glu Gln Gly Ser Met Ser Ile Pro Tyr Gln His Val
        50                  55                  60

Asn Val Pro Lys Val Asp Arg Lys Val Val Ser Leu Val Val Arg Pro
65                  70                  75                  80

Phe Ser Ser Gly Ala Phe Ser Ile Ser Gly Val Ile Ser Pro Ala His
                85                  90                  95

Ala Tyr Leu Leu Glu Cys Leu Pro Gln Leu Glu Gln Ala Met Ala Phe
                100                 105                 110

Val Ala Ser Pro Glu Ser Phe Gln Ala Ser Asp Val Ala Lys Arg Phe
            115                 120                 125

Ala Ile Lys Pro Gly Met Ser Leu Gln Asp Ala Ile Thr Ala Phe Ile
        130                 135                 140

Asn Phe Val Ser Ala Met Leu Lys Met Thr Val Thr Arg Gln Asn Phe
145                 150                 155                 160

Asp Val Ile Val Ala Glu Ile Glu Arg Leu Ala Ser Thr Ser Val Ser
                165                 170                 175

Val Arg Thr Glu Glu Ala Lys Val Ala Asp Glu Glu Leu Met Leu Phe
            180                 185                 190

Gly Leu Asp His Arg Gly Pro Gln Gln Leu Asp Val Ser Asp Ala Lys
        195                 200                 205
```

-continued

```
Gly Ile Met Lys Ala Ala Asp Ile Gln Thr Thr His Asp Val His Leu
210                 215                 220
Ala Pro Gly Val Gly Asn Ile Asp Pro Glu Ile Tyr Asn Glu Gly Arg
225                 230                 235                 240
Phe Met Phe Met Gln His Lys Pro Leu Ala Ala Asp Gln Ser Tyr Phe
                245                 250                 255
Thr Leu Glu Thr Ala Asp Tyr Phe Lys Ile Tyr Pro Thr Tyr Asp Glu
            260                 265                 270
His Asp Gly Arg Met Ala Asp Gln Lys Gln Ser Gly Leu Ile Leu Cys
        275                 280                 285
Thr Lys Asp Glu Val Leu Ala Glu Gln Thr Ile Phe Lys Leu Asp Ala
    290                 295                 300
Pro Asp Asp Lys Thr Val His Leu Leu Asp Arg Asp Asp His Val
305                 310                 315                 320
Val Ala Arg Phe Thr Lys Val Phe Ile Glu Asp Val Ala Pro Gly His
                325                 330                 335
His Ala Ala Gln Arg Ser Gly Gln Arg Ser Val Leu Asp Asp Leu Tyr
            340                 345                 350
Ala Asn Thr Gln Val Ile Ser Ile Thr Ser Ala Ala Leu Lys Trp Val
        355                 360                 365
Val Lys His Gly Val Ser Asp Gly Ile Val Asn Arg Lys Asn Val Lys
    370                 375                 380
Val Cys Val Gly Phe Asp Pro Leu Tyr Thr Leu Ser Thr His Asn Gly
385                 390                 395                 400
Val Ser Leu Cys Ala Leu Leu Met Asp Glu Lys Leu Ser Val Leu Asn
                405                 410                 415
Ser Ala Cys Arg Met Thr Leu Arg Ser Leu Met Lys Thr Gly Arg Asp
            420                 425                 430
Val Asp Ala His Arg Ala Phe Gln Arg Val Leu Ser Gln Gly Tyr Thr
        435                 440                 445
Ser Leu Met Cys Tyr Tyr His Pro Ser Arg Lys Leu Ala Tyr Gly Glu
    450                 455                 460
Val Leu Phe Leu Glu Arg Ser Asn Asp Val Thr Asp Gly Ile Lys Leu
465                 470                 475                 480
Gln Leu Asp Ala Ser Arg Gln Cys His Glu Cys Pro Val Leu Gln Gln
                485                 490                 495
Lys Val Val Glu Leu Glu Lys Gln Ile Ile Met Gln Lys Ser Ile Gln
            500                 505                 510
Ser Asp Pro Thr Pro Val Ala Leu Gln Pro Leu Leu Ser Gln Leu Arg
        515                 520                 525
Glu Leu Ser Ser Glu Val Thr Arg Leu Gln Met Glu Leu Ser Arg Ala
    530                 535                 540
Gln Ser Leu Asn Ala Gln Leu Glu Ala Asp Val Lys Ser Ala Gln Ser
545                 550                 555                 560
Cys Ser Leu Asp Met Tyr Leu Arg His Thr Cys Ile Asn Gly His
                565                 570                 575
Ala Lys Glu Asp Glu Leu Leu Asp Ala Val Arg Val Ala Pro Asp Val
            580                 585                 590
Arg Arg Glu Ile Met Glu Lys Arg Ser Glu Val Arg Gln Gly Trp Cys
        595                 600                 605
Glu Arg Ile Ser Lys Glu Ala Ala Ala Lys Cys Gln Thr Val Ile Asp
    610                 615                 620
Asp Leu Thr Leu Met Asn Gly Lys Gln Ala Gln Glu Ile Thr Glu Leu
```

```
                625                 630                 635                 640
Arg Asp Ser Ala Glu Lys Tyr Glu Lys Gln Ile Ala Glu Leu Val Ser
                    645                 650                 655

Thr Ile Thr Gln Asn Gln Ile Thr Tyr Gln Gln Glu Leu Gln Ala Leu
                    660                 665                 670

Val Ala Lys Asn Val Glu Leu Asp Ala Leu Asn Gln Arg Gln Ala Lys
                    675                 680                 685

Ser Leu Arg Ile Thr Pro Ser Leu Leu Ser Ala Thr Pro Ile Asp Ser
                    690                 695                 700

Val Asp Val Ala Asp Leu Ile Asp Phe Ser Val Pro Thr Asp Glu
                    705                 710                 715                 720

Leu

<210> SEQ ID NO 19
<211> LENGTH: 1267
<212> TYPE: PRT
<213> ORGANISM: Reovirus

<400> SEQUENCE: 19

Met Ser Ser Met Ile Leu Thr Gln Phe Gly Pro Phe Ile Glu Ser Ile
 1                   5                  10                  15

Ser Gly Ile Thr Asp Gln Ser Asn Asp Val Phe Glu Asp Ala Ala Lys
                    20                  25                  30

Ala Phe Ser Met Phe Thr Arg Ser Asp Val Tyr Lys Ala Leu Asp Glu
                    35                  40                  45

Ile Pro Phe Ser Asp Asp Ala Met Leu Pro Ile Pro Pro Thr Ile Tyr
                    50                  55                  60

Thr Lys Pro Ser His Asp Ser Tyr Tyr Tyr Ile Asp Ala Leu Asn Arg
 65                  70                  75                  80

Val Arg Arg Lys Thr Tyr Gln Gly Pro Asp Asp Val Tyr Val Pro Asn
                    85                  90                  95

Cys Ser Ile Val Glu Leu Leu Glu Pro His Glu Thr Leu Thr Ser Tyr
                    100                 105                 110

Gly Arg Leu Ser Glu Ala Ile Glu Asn Arg Ala Lys Asp Gly Asp Ser
                    115                 120                 125

Gln Ala Arg Ile Ala Thr Thr Tyr Gly Arg Ile Ala Glu Ser Gln Ala
                    130                 135                 140

Arg Gln Ile Lys Ala Pro Leu Glu Lys Phe Val Leu Ala Leu Leu Val
145                 150                 155                 160

Ala Glu Ala Gly Gly Ser Leu Tyr Asp Pro Val Leu Gln Lys Tyr Asp
                    165                 170                 175

Glu Ile Pro Asp Leu Ser His Asn Cys Pro Leu Trp Cys Phe Arg Glu
                    180                 185                 190

Ile Cys Arg His Ile Ser Gly Pro Leu Pro Asp Arg Ala Pro Tyr Leu
                    195                 200                 205

Tyr Leu Ser Ala Gly Val Phe Trp Leu Met Ser Pro Arg Met Thr Ser
                    210                 215                 220

Ala Ile Pro Pro Leu Leu Ser Asp Leu Val Asn Leu Ala Ile Leu Gln
225                 230                 235                 240

Gln Thr Ala Gly Leu Asp Pro Ser Leu Val Lys Leu Gly Val Gln Ile
                    245                 250                 255

Cys Leu His Ala Ala Ala Ser Ser Tyr Ala Trp Phe Ile Leu Lys
                    260                 265                 270

Thr Lys Ser Ile Phe Pro Gln Asn Thr Leu His Ser Met Tyr Glu Ser
                    275                 280                 285
```

-continued

```
Leu Glu Gly Gly Tyr Cys Pro Asn Leu Glu Trp Leu Glu Pro Arg Ser
    290                 295                 300
Asp Tyr Lys Phe Met Tyr Met Gly Val Met Pro Leu Ser Ala Lys Tyr
305                 310                 315                 320
Ala Arg Ser Ala Pro Ser Asn Asp Lys Lys Ala Arg Glu Leu Gly Glu
                325                 330                 335
Lys Tyr Gly Leu Ser Ser Val Val Gly Glu Leu Arg Lys Arg Thr Lys
            340                 345                 350
Thr Tyr Val Lys His Asp Phe Ala Ser Val Arg Tyr Ile Arg Asp Ala
        355                 360                 365
Met Ala Cys Thr Ser Gly Ile Phe Leu Val Arg Thr Pro Thr Glu Thr
370                 375                 380
Val Leu Gln Glu Tyr Thr Gln Ser Pro Glu Ile Lys Val Pro Ile Pro
385                 390                 395                 400
Gln Lys Asp Trp Thr Gly Pro Ile Gly Glu Ile Arg Ile Leu Lys Asp
                405                 410                 415
Thr Thr Ser Ser Ile Ala Arg Tyr Leu Tyr Arg Thr Trp Tyr Leu Ala
            420                 425                 430
Ala Ala Arg Met Ala Ala Gln Pro Arg Thr Trp Asp Pro Leu Phe Gln
        435                 440                 445
Ala Ile Met Arg Ser Gln Tyr Val Thr Ala Arg Gly Gly Ser Gly Ala
450                 455                 460
Ala Leu Arg Glu Ser Leu Tyr Ala Ile Asn Val Ser Leu Pro Asp Phe
465                 470                 475                 480
Lys Gly Leu Pro Val Lys Ala Ala Thr Lys Ile Phe Gln Ala Ala Gln
                485                 490                 495
Leu Ala Asn Leu Pro Phe Ser His Thr Ser Val Ala Ile Leu Ala Asp
            500                 505                 510
Thr Ser Met Gly Leu Arg Asn Gln Val Gln Arg Arg Pro Arg Ser Ile
        515                 520                 525
Met Pro Leu Asn Val Pro Gln Gln Gln Val Ser Ala Pro His Thr Leu
530                 535                 540
Thr Ala Asp Tyr Ile Asn Tyr His Met Asn Leu Ser Thr Thr Ser Gly
545                 550                 555                 560
Ser Ala Val Ile Glu Lys Val Ile Pro Leu Gly Val Tyr Ala Ser Ser
                565                 570                 575
Pro Pro Asn Gln Ser Ile Asn Ile Asp Ile Ser Ala Cys Asp Ala Ser
            580                 585                 590
Ile Thr Trp Asp Phe Phe Leu Ser Val Ile Met Ala Ala Ile His Glu
        595                 600                 605
Gly Val Ala Ser Ser Ile Gly Lys Pro Phe Met Gly Val Pro Ala
610                 615                 620
Ser Ile Val Asn Asp Glu Ser Val Val Gly Val Arg Ala Ala Arg Pro
625                 630                 635                 640
Ile Ser Gly Met Gln Asn Met Ile Gln His Leu Ser Lys Leu Tyr Lys
                645                 650                 655
Arg Gly Phe Ser Tyr Arg Val Asn Asp Ser Phe Ser Pro Gly Asn Asp
            660                 665                 670
Phe Thr His Met Thr Thr Thr Phe Pro Ser Gly Ser Thr Ala Thr Ser
        675                 680                 685
Thr Glu His Thr Ala Asn Asn Ser Thr Met Met Glu Thr Phe Leu Thr
690                 695                 700
Val Trp Gly Pro Glu His Thr Asp Asp Pro Asp Val Leu Arg Leu Met
```

```
              705                 710                 715                 720
Lys Ser Leu Thr Ile Gln Arg Asn Tyr Val Cys Gln Gly Asp Asp Gly
                725                 730                 735
Leu Met Ile Ile Asp Gly Thr Thr Ala Gly Lys Val Asn Ser Glu Thr
                740                 745                 750
Ile Gln Lys Met Leu Glu Leu Ile Ser Lys Tyr Gly Glu Glu Phe Gly
                755                 760                 765
Trp Lys Tyr Asp Ile Ala Tyr Asp Gly Thr Ala Glu Tyr Leu Lys Leu
                770                 775                 780
Tyr Phe Ile Phe Gly Cys Arg Ile Pro Asn Leu Ser Arg His Pro Ile
785                 790                 795                 800
Val Gly Lys Glu Arg Ala Asn Ser Ser Ala Glu Glu Pro Trp Pro Ala
                805                 810                 815
Ile Leu Asp Gln Ile Met Gly Val Phe Phe Asn Gly Val His Asp Gly
                820                 825                 830
Leu Gln Trp Gln Arg Trp Ile Arg Tyr Ser Trp Ala Leu Cys Cys Ala
                835                 840                 845
Phe Ser Arg Gln Arg Thr Met Ile Gly Glu Ser Val Gly Tyr Leu Gln
850                 855                 860
Tyr Pro Met Trp Ser Phe Val Tyr Trp Gly Leu Pro Leu Val Lys Ala
865                 870                 875                 880
Phe Gly Ser Asp Pro Trp Ile Phe Ser Trp Tyr Met Pro Thr Gly Asp
                885                 890                 895
Leu Gly Met Tyr Ser Trp Ile Ser Leu Ile Arg Pro Leu Met Thr Arg
                900                 905                 910
Trp Met Val Ala Asn Gly Tyr Val Thr Asp Arg Cys Ser Pro Val Phe
                915                 920                 925
Gly Asn Ala Asp Tyr Arg Arg Cys Phe Asn Glu Leu Lys Leu Tyr Gln
                930                 935                 940
Gly Tyr Tyr Met Ala Gln Leu Pro Arg Asn Pro Lys Lys Ser Gly Arg
945                 950                 955                 960
Ala Ala Pro Arg Glu Val Arg Glu Gln Phe Thr Gln Ala Leu Ser Asp
                965                 970                 975
Tyr Leu Leu Gln Asn Pro Glu Leu Lys Ser Arg Val Leu Arg Gly Arg
                980                 985                 990
Ser Glu Trp Glu Lys Tyr Gly Ala Gly Ile Ile His Asn Pro Pro Ser
                995                 1000                1005
Leu Phe Asp Val Pro His Lys Trp Tyr Gln Gly Ala Gln Glu Ala Ala
                1010                1015                1020
Ile Ala Thr Arg Glu Glu Leu Ala Glu Met Asp Glu Thr Leu Met Arg
1025                1030                1035                1040
Ala Arg Arg His Arg Tyr Ser Ser Phe Ser Lys Leu Leu Glu Ala Tyr
                1045                1050                1055
Leu Leu Val Lys Trp Arg Met Cys Glu Ala Arg Glu Pro Ser Val Asp
                1060                1065                1070
Leu Arg Leu Pro Leu Cys Ala Gly Ile Asp Pro Leu Asn Ser Asp Pro
                1075                1080                1085
Phe Leu Lys Met Val Ser Val Gly Pro Met Leu Gln Ser Thr Arg Lys
                1090                1095                1100
Tyr Phe Ala Gln Thr Leu Phe Met Ala Lys Thr Val Ser Gly Leu Asp
1105                1110                1115                1120
Val Asn Ala Ile Asp Ser Ala Leu Leu Arg Leu Arg Thr Leu Gly Ala
                1125                1130                1135
```

-continued

```
Asp Lys Lys Ala Leu Thr Ala Gln Leu Leu Met Val Gly Leu Gln Glu
        1140                1145                1150

Ser Glu Ala Asp Ala Leu Ala Gly Lys Ile Met Leu Gln Asp Val Asn
            1155                1160                1165

Thr Val Gln Leu Ala Arg Val Val Asn Leu Ala Val Pro Asp Thr Trp
        1170                1175                1180

Met Ser Leu Asp Phe Asp Ser Met Phe Lys His His Val Lys Leu Leu
1185                1190                1195                1200

Pro Lys Asp Gly Arg His Leu Asn Thr Asp Ile Pro Pro Arg Met Gly
            1205                1210                1215

Trp Leu Arg Ala Ile Leu Arg Phe Leu Gly Ala Gly Met Val Met Thr
        1220                1225                1230

Ala Thr Gly Val Ala Val Asp Ile Tyr Leu Glu Asp Ile His Gly Gly
            1235                1240                1245

Gly Arg Ser Leu Gly Gln Arg Phe Met Thr Trp Met Arg Gln Glu Gly
        1250                1255                1260

Arg Ser Ala
1265

<210> SEQ ID NO 20
<211> LENGTH: 1289
<212> TYPE: PRT
<213> ORGANISM: Reovirus

<400> SEQUENCE: 20

Met Ala Asn Val Trp Gly Val Arg Leu Ala Asp Ser Leu Ser Ser Pro
1               5                   10                  15

Thr Ile Glu Thr Arg Thr Arg Gln Tyr Thr Leu His Asp Leu Cys Ser
            20                  25                  30

Asp Leu Asp Ala Asn Pro Gly Arg Glu Pro Trp Lys Pro Leu Arg Asn
        35                  40                  45

Gln Arg Thr Asn Asn Ile Val Ala Val Gln Leu Phe Arg Pro Leu Gln
    50                  55                  60

Gly Leu Val Leu Asp Thr Gln Leu Tyr Gly Phe Pro Gly Ala Phe Asp
65                  70                  75                  80

Asp Trp Glu Arg Phe Met Arg Glu Lys Leu Arg Val Leu Lys Tyr Glu
                85                  90                  95

Val Leu Arg Ile Tyr Pro Ile Ser Asn Tyr Ser Asn Glu His Val Asn
            100                 105                 110

Val Phe Val Ala Asn Ala Leu Val Gly Ala Phe Leu Ser Asn Gln Ala
        115                 120                 125

Phe Tyr Asp Leu Leu Pro Leu Leu Ile Ile Asn Asp Thr Met Ile Gly
    130                 135                 140

Asp Leu Leu Gly Thr Gly Ala Ser Leu Ser Gln Phe Phe Gln Ser His
145                 150                 155                 160

Gly Asp Val Leu Glu Val Ala Ala Gly Arg Lys Tyr Leu Gln Met Glu
                165                 170                 175

Asn Tyr Ser Asn Asp Asp Asp Pro Pro Leu Phe Ala Lys Asp Leu
            180                 185                 190

Ser Asp Tyr Ala Lys Ala Phe Tyr Ser Asp Thr Tyr Glu Val Leu Asp
        195                 200                 205

Arg Phe Phe Trp Thr His Asp Ser Ser Ala Gly Val Leu Val His Tyr
    210                 215                 220

Asp Lys Pro Thr Asn Gly His His Tyr Leu Leu Gly Thr Leu Thr Gln
225                 230                 235                 240
```

```
Met Val Ser Ala Pro Tyr Ile Ile Asn Ala Thr Asp Ala Met Leu
                245                 250                 255

Leu Glu Ser Cys Leu Glu Gln Phe Ser Ala Asn Val Arg Ala Arg Pro
            260                 265                 270

Ala Gln Pro Val Thr Arg Leu Asp Gln Cys Tyr His Leu Arg Trp Gly
        275                 280                 285

Ala Gln Tyr Val Gly Glu Asp Ser Leu Thr Tyr Arg Leu Gly Val Leu
    290                 295                 300

Ser Leu Leu Ala Thr Asn Gly Tyr Gln Leu Ala Arg Pro Ile Pro Arg
305                 310                 315                 320

Gln Leu Thr Asn Arg Trp Leu Ser Ser Phe Val Ser Gln Ile Met Ser
                325                 330                 335

Asp Gly Val Asn Glu Thr Pro Leu Trp Pro Gln Glu Arg Tyr Val Gln
            340                 345                 350

Ile Ala Tyr Asp Ser Pro Ser Val Val Asp Gly Ala Thr Gln Tyr Gly
        355                 360                 365

Tyr Val Arg Lys Asn Gln Leu Arg Leu Gly Met Arg Ile Ser Ala Leu
    370                 375                 380

Gln Ser Leu Ser Asp Thr Pro Ser Pro Val Gln Trp Leu Pro Gln Tyr
385                 390                 395                 400

Thr Ile Asp Gln Ala Ala Met Asp Glu Gly Asp Leu Met Val Ser Arg
                405                 410                 415

Leu Thr Gln Leu Pro Leu Arg Pro Asp Tyr Gly Asn Ile Trp Val Gly
            420                 425                 430

Asp Ala Leu Ser Tyr Tyr Val Asp Tyr Asn Arg Ser His Arg Val Val
        435                 440                 445

Leu Ser Ser Glu Leu Pro Gln Leu Pro Asp Thr Tyr Phe Asp Gly Asp
450                 455                 460

Glu Gln Tyr Gly Arg Ser Leu Phe Ser Leu Ala Arg Lys Ile Gly Asp
465                 470                 475                 480

Arg Ser Leu Val Lys Asp Thr Ala Val Leu Lys His Ala Tyr Gln Ala
                485                 490                 495

Ile Asp Pro Asn Thr Gly Lys Glu Tyr Leu Arg Ser Arg Gln Ser Val
            500                 505                 510

Ala Tyr Phe Gly Ala Ser Ala Gly His Ser Gly Ala Asp Gln Pro Leu
        515                 520                 525

Val Ile Glu Pro Trp Ile Gln Gly Lys Ile Ser Gly Val Pro Pro
530                 535                 540

Ser Ser Val Arg Gln Phe Gly Tyr Asp Val Ala Arg Gly Ala Ile Val
545                 550                 555                 560

Asp Leu Ala Arg Pro Phe Pro Ser Gly Asp Tyr Gln Phe Val Tyr Ser
                565                 570                 575

Asp Val Asp Gln Val Val Asp Gly His Asp Asp Leu Ser Ile Ser Ser
            580                 585                 590

Gly Leu Val Glu Ser Leu Leu Ser Ser Cys Met His Ala Thr Ala Pro
        595                 600                 605

Gly Gly Ser Phe Val Val Lys Ile Asn Phe Pro Thr Arg Pro Val Trp
    610                 615                 620

His Tyr Ile Glu Gln Lys Ile Leu Pro Asn Ile Thr Ser Tyr Met Leu
625                 630                 635                 640

Ile Lys Pro Phe Val Thr Asn Asn Val Glu Leu Phe Phe Val Ala Phe
                645                 650                 655

Gly Val His Gln His Ser Ser Leu Thr Trp Thr Ser Gly Val Tyr Phe
            660                 665                 670
```

```
Phe Leu Val Asp His Phe Tyr Arg Tyr Glu Thr Leu Ser Thr Ile Ser
            675                 680                 685

Arg Gln Leu Pro Ser Phe Gly Tyr Val Asp Asp Gly Ser Ser Val Thr
        690                 695                 700

Gly Ile Glu Thr Ile Ser Ile Glu Asn Pro Gly Phe Ser Asn Met Thr
705                 710                 715                 720

Gln Ala Ala Arg Ile Gly Ile Ser Gly Leu Cys Ala Asn Val Gly Asn
                725                 730                 735

Ala Arg Lys Ser Ile Ala Ile Tyr Glu Ser His Gly Ala Arg Val Leu
            740                 745                 750

Thr Ile Thr Ser Arg Arg Ser Pro Ala Ser Ala Arg Arg Lys Ser Arg
        755                 760                 765

Leu Arg Tyr Leu Pro Leu Ile Asp Pro Arg Ser Leu Glu Val Gln Ala
        770                 775                 780

Arg Thr Ile Leu Pro Ala Asp Pro Val Leu Phe Glu Asn Val Ser Gly
785                 790                 795                 800

Ala Ser Pro His Val Cys Leu Thr Met Met Tyr Asn Phe Glu Val Ser
                805                 810                 815

Ser Ala Val Tyr Asp Gly Asp Val Val Leu Asp Leu Gly Thr Gly Pro
            820                 825                 830

Glu Ala Lys Ile Leu Glu Leu Ile Pro Ala Thr Ser Pro Val Thr Cys
            835                 840                 845

Val Asp Ile Arg Pro Thr Ala Gln Pro Ser Gly Cys Trp Asn Val Arg
850                 855                 860

Thr Thr Phe Leu Glu Leu Asp Tyr Leu Ser Asp Gly Trp Ile Thr Gly
865                 870                 875                 880

Val Arg Gly Asp Ile Val Thr Cys Met Leu Ser Leu Gly Ala Ala Ala
                885                 890                 895

Ala Gly Lys Ser Met Thr Phe Asp Ala Ala Phe Gln Gln Leu Ile Lys
            900                 905                 910

Val Leu Ser Lys Ser Thr Ala Asn Val Val Leu Val Gln Val Asn Cys
        915                 920                 925

Pro Thr Asp Val Val Arg Ser Ile Lys Gly Tyr Leu Glu Ile Asp Ser
        930                 935                 940

Thr Asn Lys Arg Tyr Arg Phe Pro Lys Phe Gly Arg Asp Glu Pro Tyr
945                 950                 955                 960

Ser Asp Met Asp Ala Leu Glu Lys Ile Cys Arg Thr Ala Trp Pro Asn
                965                 970                 975

Cys Ser Ile Thr Trp Val Pro Leu Ser Tyr Asp Leu Arg Trp Thr Arg
            980                 985                 990

Leu Ala Leu Leu Glu Ser Thr Thr Leu Ser Ser Ala Ser Ile Arg Ile
        995                 1000                1005

Ala Glu Leu Met Tyr Lys Tyr Met Pro Ile Met Arg Ile Asp Ile His
        1010                1015                1020

Gly Leu Pro Met Glu Lys Arg Gly Asn Phe Ile Val Gly Gln Asn Cys
1025                1030                1035                1040

Ser Leu Val Ile Pro Gly Phe Asn Ala Gln Asp Val Phe Asn Cys Tyr
                1045                1050                1055

Phe Asn Ser Ala Leu Ala Phe Ser Thr Glu Asp Val Asn Ala Ala Met
            1060                1065                1070

Ile Pro Gln Val Ser Ala Gln Phe Asp Ala Thr Lys Gly Glu Trp Thr
        1075                1080                1085

Leu Asp Met Val Phe Ser Asp Ala Gly Ile Tyr Thr Met Gln Ala Leu
```

```
                1090              1095              1100
Val Gly Ser Asn Ala Asn Pro Val Ser Leu Gly Ser Phe Val Val Asp
1105              1110              1115              1120

Ser Pro Asp Val Asp Ile Thr Asp Ala Trp Pro Ala Gln Leu Asp Phe
            1125              1130              1135

Thr Ile Ala Gly Thr Asp Val Asp Ile Thr Val Asn Pro Tyr Tyr Arg
        1140              1145              1150

Leu Met Thr Phe Val Arg Ile Asp Gly Gln Trp Gln Ile Ala Asn Pro
            1155              1160              1165

Asp Lys Phe Gln Phe Phe Ser Ser Ala Ser Gly Thr Leu Val Met Asn
        1170              1175              1180

Val Lys Leu Asp Ile Ala Asp Lys Tyr Leu Leu Tyr Tyr Ile Arg Asp
1185              1190              1195              1200

Val Gln Ser Arg Asp Val Gly Phe Tyr Ile Gln His Pro Leu Gln Leu
            1205              1210              1215

Leu Asn Thr Ile Thr Leu Pro Thr Asn Glu Asp Leu Phe Leu Ser Ala
        1220              1225              1230

Pro Asp Met Arg Glu Trp Ala Val Lys Glu Ser Gly Asn Thr Ile Cys
            1235              1240              1245

Ile Leu Asn Ser Gln Gly Phe Val Leu Pro Gln Asp Trp Asp Val Leu
        1250              1255              1260

Thr Asp Thr Ile Ser Trp Ser Pro Ser Ile Pro Thr Tyr Ile Val Pro
1265              1270              1275              1280

Pro Gly Asp Tyr Thr Leu Thr Pro Leu
            1285

<210> SEQ ID NO 21
<211> LENGTH: 1275
<212> TYPE: PRT
<213> ORGANISM: Reovirus

<400> SEQUENCE: 21

Met Lys Arg Ile Pro Arg Lys Thr Lys Gly Lys Ser Ser Gly Lys Gly
1               5                   10                  15

Asn Asp Ser Thr Glu Arg Ala Asp Asp Gly Ser Ser Gln Leu Arg Asp
            20                  25                  30

Lys Gln Asn Asn Lys Ala Gly Pro Ala Thr Thr Glu Pro Gly Thr Ser
        35                  40                  45

Asn Arg Glu Gln Tyr Lys Ala Arg Pro Gly Ile Ala Ser Val Gln Arg
    50                  55                  60

Ala Thr Glu Ser Ala Glu Met Pro Met Lys Asn Asn Asp Glu Gly Thr
65                  70                  75                  80

Pro Asp Lys Lys Gly Asn Thr Lys Gly Asp Leu Val Asn Glu His Ser
            85                  90                  95

Glu Ala Lys Asp Glu Ala Asp Glu Ala Thr Lys Lys Gln Ala Lys Asp
        100                 105                 110

Thr Asp Lys Ser Lys Ala Gln Val Thr Tyr Ser Asp Thr Gly Ile Asn
    115                 120                 125

Asn Ala Asn Glu Leu Ser Arg Ser Gly Asn Val Asp Asn Glu Gly Gly
130                 135                 140

Ser Asn Gln Lys Pro Met Ser Thr Arg Ile Ala Glu Ala Thr Ser Ala
145                 150                 155                 160

Ile Val Ser Lys His Pro Ala Arg Val Gly Leu Pro Pro Thr Ala Ser
            165                 170                 175

Ser Gly His Gly Tyr Gln Cys His Val Cys Ser Ala Val Leu Phe Ser
```

```
                180                 185                 190
Pro Leu Asp Leu Asp Ala His Val Ala Ser His Gly Leu His Gly Asn
            195                 200                 205

Met Thr Leu Thr Ser Ser Asp Ile Gln Arg His Ile Thr Glu Phe Ile
            210                 215                 220

Ser Ser Trp Gln Asn His Pro Ile Val Gln Val Ser Ala Asp Val Glu
225                 230                 235                 240

Asn Lys Lys Thr Ala Gln Leu Leu His Ala Asp Thr Pro Arg Leu Val
                245                 250                 255

Thr Trp Asp Ala Gly Leu Cys Thr Ser Phe Lys Ile Val Pro Ile Val
            260                 265                 270

Pro Ala Gln Val Pro Gln Asp Val Leu Ala Tyr Thr Phe Phe Thr Ser
            275                 280                 285

Ser Tyr Ala Ile Gln Ser Pro Phe Pro Glu Ala Ala Val Ser Arg Ile
            290                 295                 300

Val Val His Thr Arg Trp Ala Ser Asn Val Asp Phe Asp Arg Asp Ser
305                 310                 315                 320

Ser Val Ile Met Ala Pro Pro Thr Glu Asn Asn Ile His Leu Phe Lys
                325                 330                 335

Gln Leu Leu Asn Thr Glu Thr Leu Ser Val Arg Gly Ala Asn Pro Leu
            340                 345                 350

Met Phe Arg Ala Asn Val Leu His Met Leu Leu Glu Phe Val Leu Asp
            355                 360                 365

Asn Leu Tyr Leu Asn Arg His Thr Gly Phe Ser Gln Asp His Thr Pro
            370                 375                 380

Phe Thr Glu Gly Ala Asn Leu Arg Ser Leu Pro Gly Pro Asp Ala Glu
385                 390                 395                 400

Lys Trp Tyr Ser Ile Met Tyr Pro Thr Arg Met Gly Thr Pro Asn Val
                405                 410                 415

Ser Lys Ile Cys Asn Phe Val Ala Ser Cys Val Arg Asn Arg Val Gly
            420                 425                 430

Arg Phe Asp Arg Ala Gln Met Met Asn Gly Ala Met Ser Glu Trp Val
            435                 440                 445

Asp Val Phe Glu Thr Ser Asp Ala Leu Thr Val Ser Ile Arg Gly Arg
450                 455                 460

Trp Met Ala Arg Leu Ala Arg Met Asn Ile Asn Pro Thr Glu Ile Glu
465                 470                 475                 480

Trp Ala Leu Thr Glu Cys Ala Gln Gly Tyr Val Thr Val Thr Ser Pro
                485                 490                 495

Tyr Ala Pro Ser Val Asn Arg Leu Met Pro Tyr Arg Ile Ser Asn Ala
            500                 505                 510

Glu Arg Gln Ile Ser Gln Ile Ile Arg Ile Met Asn Ile Gly Asn Asn
            515                 520                 525

Ala Thr Val Ile Gln Pro Val Leu Gln Asp Ile Ser Val Leu Leu Gln
            530                 535                 540

Arg Ile Ser Pro Leu Gln Ile Asp Pro Thr Ile Ile Ser Asn Thr Met
545                 550                 555                 560

Ser Thr Val Ser Glu Ser Thr Thr Gln Thr Leu Ser Pro Ala Ser Ser
                565                 570                 575

Ile Leu Gly Lys Leu Arg Pro Ser Asn Ser Asp Phe Ser Ser Phe Arg
            580                 585                 590

Val Ala Leu Ala Gly Trp Leu Tyr Asn Gly Val Val Thr Thr Val Ile
            595                 600                 605
```

```
Asp Asp Ser Ser Tyr Pro Lys Asp Gly Gly Ser Val Thr Ser Leu Glu
        610                 615                 620

Asn Leu Trp Asp Phe Phe Ile Leu Ala Leu Ala Leu Pro Leu Thr Thr
625                 630                 635                 640

Asp Pro Cys Ala Pro Val Lys Ala Phe Met Thr Leu Ala Asn Met Met
                645                 650                 655

Val Gly Phe Glu Thr Ile Pro Met Asp Asn Gln Ile Tyr Thr Gln Ser
                660                 665                 670

Arg Arg Ala Ser Ala Phe Ser Thr Pro His Thr Trp Pro Arg Cys Phe
        675                 680                 685

Met Asn Ile Gln Leu Ile Ser Pro Ile Asp Ala Pro Ile Leu Arg Gln
        690                 695                 700

Trp Ala Glu Ile Ile His Arg Tyr Trp Pro Asn Pro Ser Gln Ile Arg
705                 710                 715                 720

Tyr Gly Ala Pro Asn Val Phe Gly Ser Ala Asn Leu Phe Thr Pro Pro
                725                 730                 735

Glu Val Leu Leu Leu Pro Ile Asp His Gln Pro Ala Asn Val Thr Thr
                740                 745                 750

Pro Thr Leu Asp Phe Thr Asn Glu Leu Thr Asn Trp Arg Ala Arg Val
        755                 760                 765

Cys Glu Leu Met Lys Asn Leu Val Asp Asn Gln Arg Tyr Gln Pro Gly
        770                 775                 780

Trp Thr Gln Ser Leu Val Ser Ser Met Arg Gly Thr Leu Asp Lys Leu
785                 790                 795                 800

Lys Leu Ile Lys Ser Met Thr Pro Met Tyr Leu Gln Gln Leu Ala Pro
                805                 810                 815

Val Glu Leu Ala Val Ile Ala Pro Met Leu Pro Phe Pro Pro Phe Gln
                820                 825                 830

Val Pro Tyr Val Arg Leu Asp Arg Asp Arg Val Pro Thr Met Val Gly
                835                 840                 845

Val Thr Arg His Ser Arg Asp Thr Ile Thr Gln Pro Ala Leu Ser Leu
        850                 855                 860

Ser Thr Thr Asn Thr Thr Val Gly Val Pro Leu Ala Leu Asp Ala Arg
865                 870                 875                 880

Ala Ile Thr Val Ala Leu Leu Ser Gly Lys Tyr Pro Pro Asp Leu Val
                885                 890                 895

Thr Asn Val Trp Tyr Ala Asp Ala Ile Tyr Pro Met Tyr Ala Asp Thr
                900                 905                 910

Glu Val Phe Ser Asn Leu Gln Arg Asp Met Ile Thr Cys Glu Ala Val
        915                 920                 925

Gln Thr Leu Val Thr Leu Val Ala Gln Ile Ser Glu Thr Gln Tyr Pro
        930                 935                 940

Val Asp Arg Tyr Leu Asp Trp Ile Pro Ser Leu Arg Ala Ser Ala Ala
945                 950                 955                 960

Thr Ala Ala Thr Phe Ala Glu Trp Val Asn Thr Ser Met Lys Thr Ala
                965                 970                 975

Phe Asp Leu Ser Asp Met Leu Leu Glu Pro Leu Leu Ser Gly Asp Pro
        980                 985                 990

Arg Met Thr Gln Leu Ala Ile Gln Tyr Gln Gln Tyr Asn Gly Arg Thr
        995                 1000                1005

Phe Asn Ile Ile Pro Glu Met Pro Gly Ser Val Ile Ala Asp Cys Val
        1010                1015                1020

Gln Leu Thr Ala Glu Val Phe Asn His Glu Tyr Asn Leu Phe Gly Ile
1025                1030                1035                1040
```

```
Ala Arg Gly Asp Ile Ile Ile Gly Arg Val Gln Ser Thr His Leu Trp
            1045            1050                1055

Ser Pro Leu Ala Pro Pro Pro Asp Leu Val Phe Asp Arg Asp Thr Pro
            1060            1065                1070

Gly Val His Ile Phe Gly Arg Asp Cys Arg Ile Ser Phe Gly Met Asn
            1075            1080                1085

Gly Ala Ala Pro Met Ile Arg Asp Glu Thr Gly Leu Met Val Pro Phe
            1090            1095                1100

Glu Gly Asn Trp Ile Phe Pro Leu Ala Leu Trp Gln Met Asn Thr Arg
1105            1110            1115                1120

Tyr Phe Asn Gln Gln Phe Asp Ala Trp Ile Lys Thr Gly Glu Leu Arg
                1125            1130                1135

Ile Arg Ile Glu Met Gly Ala Tyr Pro Tyr Met Leu His Tyr Tyr Asp
            1140            1145                1150

Pro Arg Gln Tyr Ala Asn Ala Trp Asn Leu Thr Ser Ala Trp Leu Glu
            1155            1160                1165

Glu Ile Thr Pro Thr Ser Ile Pro Ser Val Pro Phe Met Val Pro Ile
    1170            1175            1180

Ser Ser Asp His Asp Ile Ser Ser Ala Pro Ala Val Gln Tyr Ile Ile
1185            1190            1195                1200

Ser Thr Glu Tyr Asn Asp Arg Ser Leu Phe Cys Thr Asn Ser Ser Ser
            1205            1210            1215

Pro Gln Thr Ile Ala Gly Pro Asp Lys His Ile Pro Val Glu Arg Tyr
            1220            1225            1230

Asn Ile Leu Thr Asn Pro Asp Ala Pro Pro Thr Gln Ile Gln Leu Pro
            1235            1240            1245

Glu Val Val Asp Leu Tyr Asn Val Val Thr Arg Tyr Ala Tyr Glu Thr
    1250            1255            1260

Pro Pro Ile Thr Ala Val Val Met Gly Val Pro
1265            1270            1275
```